US009480392B2

(12) United States Patent
Bae et al.

(10) Patent No.: US 9,480,392 B2
(45) Date of Patent: Nov. 1, 2016

(54) ULTRA-WIDE RANGE OBSERVATION ENDOSCOPE APPARATUS

(71) Applicant: Samsung Electronics Co., Ltd., Gyeonggi-do (KR)

(72) Inventors: Jae-Cheol Bae, Gyeonggi-do (KR); Tae-Kyung Kim, Seoul (KR)

(73) Assignee: Samsung Electronics Co., Ltd (KR)

( * ) Notice: Subject to any disclaimer, the term of this patent is extended or adjusted under 35 U.S.C. 154(b) by 415 days.

(21) Appl. No.: 14/086,358

(22) Filed: Nov. 21, 2013

(65) Prior Publication Data

US 2014/0142381 A1 May 22, 2014

(30) Foreign Application Priority Data

Nov. 21, 2012 (KR) ........................ 10-2012-0132501

(51) Int. Cl.
*A61B 1/00* (2006.01)
*A61B 1/04* (2006.01)
*A61B 1/06* (2006.01)
*G02B 23/24* (2006.01)

(52) U.S. Cl.
CPC ........ *A61B 1/00181* (2013.01); *A61B 1/00177* (2013.01); *G02B 23/243* (2013.01); *G02B 23/2484* (2013.01); *A61B 1/00188* (2013.01)

(58) Field of Classification Search
CPC .......... A61B 1/00177; A61B 1/00181; A61B 1/00188; G02B 23/243; G02B 23/2484; G02B 23/2415; G02B 23/2407; G02B 23/2446; G02B 23/2453
USPC ....... 600/103, 109, 111, 129, 130, 160, 166, 600/176; 348/45, 65; 356/241.5; 359/462, 359/362–363
See application file for complete search history.

(56) References Cited

U.S. PATENT DOCUMENTS

| | | | |
|---|---|---|---|
| 2007/0055100 A1* | 3/2007 | Kato | A61B 1/00096 600/109 |
| 2009/0273666 A1* | 11/2009 | Konno | H04N 5/2251 348/65 |
| 2009/0278920 A1 | 11/2009 | Kamo | |
| 2012/0147164 A1* | 6/2012 | Sasamoto | A61B 1/00188 348/65 |
| 2012/0162486 A1* | 6/2012 | Asakura | G02B 3/10 348/241 |
| 2013/0155212 A1* | 6/2013 | Kamo | G02B 23/243 348/65 |
| 2013/0217965 A1* | 8/2013 | Sasamoto | G02B 7/08 600/109 |

FOREIGN PATENT DOCUMENTS

| | | |
|---|---|---|
| JP | 10288742 | 10/1998 |
| JP | 11125773 | 5/1999 |
| JP | 2004145578 | 5/2004 |
| JP | 2009276371 | 11/2009 |

* cited by examiner

*Primary Examiner* — John P Leubecker
*Assistant Examiner* — Arnaldo Torres Diaz
(74) *Attorney, Agent, or Firm* — The Farrell Law Firm, P.C.

(57) ABSTRACT

An endoscope apparatus including a first optical system and a second optical system is provided. The first optical system includes a first lens system configured to form a first optical image of a first object and a first image sensor configured to convert the first optical image into first image data and output the first image data. The second optical system includes a second lens system configured to form a second optical image of a second object and a second image sensor configured to convert the second optical image into second image data and output the second image data.

10 Claims, 20 Drawing Sheets

ULTRA-WIDE RANGE OBSERVATION ENDOSCOPE APPARATUS

PRIORITY

This application claims priority under 35 U.S.C. §119(a) to a Korean Patent Application filed in the Korean Intellectual Property Office on Nov. 21, 2012 and assigned Serial No. 10-2012-0132501, the entire disclosure of which is incorporated herein by reference.

BACKGROUND OF THE INVENTION

1. Field of the Invention

The present invention generally relates to an endoscope apparatus, and more particularly, to a colonoscope apparatus.

2. Description of the Related Art

An endoscope apparatus may be used to screen, that is, capture and examine, the interior of a large intestine to discover lesions in the large intestine.

FIG. 1 is a diagram describing screening of the interior of a large intestine by using a general endoscope apparatus 10. Referring to FIG. 1, the endoscope apparatus 10 includes a front-view optical system capable of imaging an object in front of the endoscope, and a field-of-view 11 of the front-view optical system is limited to the front of the endoscope. An observer moves the endoscope apparatus 10 backward to screen an interior 21 of a large intestine 20.

As illustrated in FIG. 1, if a lesion 30 is occluded by a curved portion 22 of the large intestine, the lesion 30 is out of the field-of-view 11 of the endoscope apparatus 10, and thus fails to be detected.

When existence of a lesion is determined merely with a front-view or front-view-observation optical system, it is not easy to detect a lesion occluded by a curved portion of a large intestine. Moreover, to observe the lesion occluded by the curved portion and observe the lesion in detail within the field of view of the endoscope apparatus, a front end portion of the endoscope apparatus may be often bent.

Therefore, a need exists for an endoscope apparatus capable of easily detecting a lesion, making it easy to observe in detail a lesion without bending of the endoscope apparatus, and minimizing a diameter of a front end portion of the endoscope apparatus.

SUMMARY OF THE INVENTION

An aspect of the present invention is to address at least the above-mentioned problems and/or disadvantages and to provide at least the advantages described below. Accordingly, an aspect of the present invention provides an endoscope apparatus that provides an ultra-wide range observation optical system for observing a lesion situated in a curved portion of a wall in a tube of a large intestine, considers arrangement of a capturing region and the number of pixels of an image sensor of the observation optical system to facilitate detection of a lesion in screening, makes it easy to observe a lesion in a magnified form based on focal lengths, viewing angles, and Depths of Field (DoFs) of a front-view optical system and a side-view optical system, and reduces a diameter of a front end portion of the endoscope apparatus.

In accordance with an aspect of the present invention, there is provided an endoscope apparatus including a first optical system including a first lens system configured to form a first optical image of a first object and a first image sensor configured to convert the first optical image into first image data and output the first image data and a second optical system including a second lens system configured to form a second optical image of a second object and a second image sensor configured to convert the second optical image into second image data and output the second image data, in which the first optical system satisfies a condition of $350<IH1/P1<800$ and $0.95<IH1/EFL1<1.3$, the second optical system satisfies a condition of $250<IH2/P2<600$ and $0.7<IH2/EFL2<1.2$, IH1 denotes a maximum image height on an image surface of the first image sensor, IH2 denotes a maximum image height on an image surface of the second image sensor, P1 denotes a pixel pitch of the first image sensor, P2 denotes a pixel pitch of the second image sensor, EFL1 denotes a focal length of the first optical system, and EFL2 denotes a focal length of the second optical system.

In accordance with another aspect of the present invention, there is provided an endoscope apparatus including a first optical system, which includes a first lens system configured to form a first optical image of a first object and a first image sensor configured to convert the first optical image into first image data and output the first image data, and a second optical system, which includes a second lens system configured to form a second optical image of a second object and a second image sensor configured to convert the second optical image into second image data and output the second image data, in which the endoscope apparatus satisfies a condition of $R2 > R3 > R1$, and R1 denotes a reciprocal of a minimum width of a pair of black and white lines that are recognizable by the first optical system at an object distance of 50 mm, R2 denotes a reciprocal of a minimum width of a pair of black and white lines that are recognizable by the first optical system at an object distance of 30 mm, and R3 denotes a reciprocal of a minimum width of a pair of black and white lines that are recognizable by the second optical system at the object distance of 30 mm.

BRIEF DESCRIPTION OF THE DRAWINGS

The above and other features and advantages of embodiments of the present invention will be more apparent from the following detailed description taken in conjunction with the accompanying drawings, in which.

Throughout the drawings, like reference numerals will be understood to refer to like parts, components, and structures.

DETAILED DESCRIPTION OF EMBODIMENTS OF THE INVENTION

Figure 1:
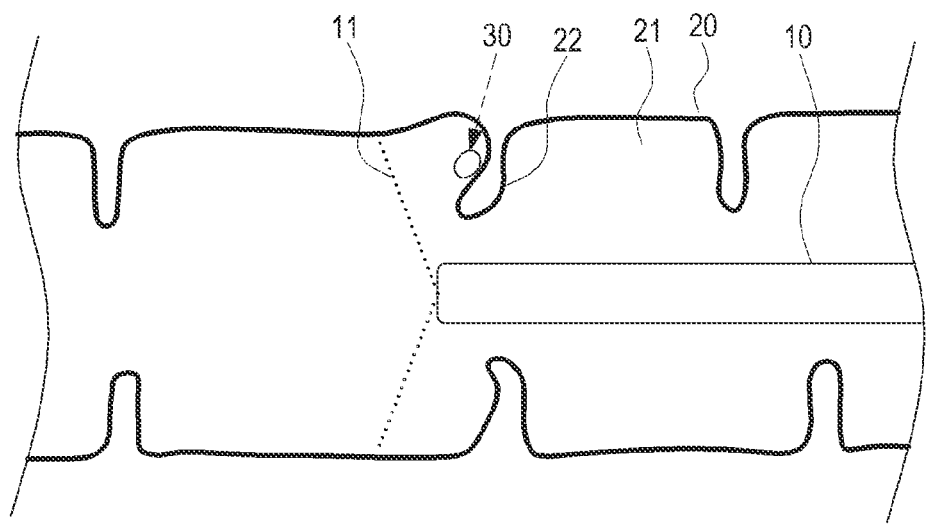
FIG. 1 is a diagram describing screening of an interior of a large intestine by using a general endoscope apparatus.

Hereinafter, the present invention may be practiced in various forms and in accordance with one or more exemplary embodiments that may or may be disclosed herein. Descriptions of embodiments of the present invention are described in detail accompanied by illustrations of the particular embodiments shown in the drawings. However, the description and illustrations do not constitute a limit to claimed scope of the invention, nor to the particular embodiments, and the present invention should be construed as including all the changes, equivalents, and substitutions included in the spirit and scope of the present invention.

Although ordinal numbers such as "first", "second", and so forth will be used to describe various components, those components are not limited by the terms, or the order of such terms. The terms are used only for distinguishing one component from another component. For example, a first component may be referred to as a second component and likewise, a second component may also be referred to as a first component, without departing from the teaching of the inventive concept. The term "and/or" used herein includes any and all combinations of one or more of the associated listed items.

The terminology used herein is for the purpose of describing embodiments only and is not intended to be limiting of embodiments. As used herein, the singular forms are intended to include the plural forms as well, unless the context clearly indicates otherwise. It will be further understood that the terms "comprises" and/or "has" when used in this specification, specify the presence of stated feature, number, step, operation, component, element, or a combination thereof but do not preclude the presence or addition of one or more other features, numbers, steps, operations, components, elements, or combinations thereof.

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the specification with the context of the relevant art as understood by the artisan at the time of invention and will not be interpreted in an idealized or overly formal sense unless expressly so defined herein.

Figure 2:
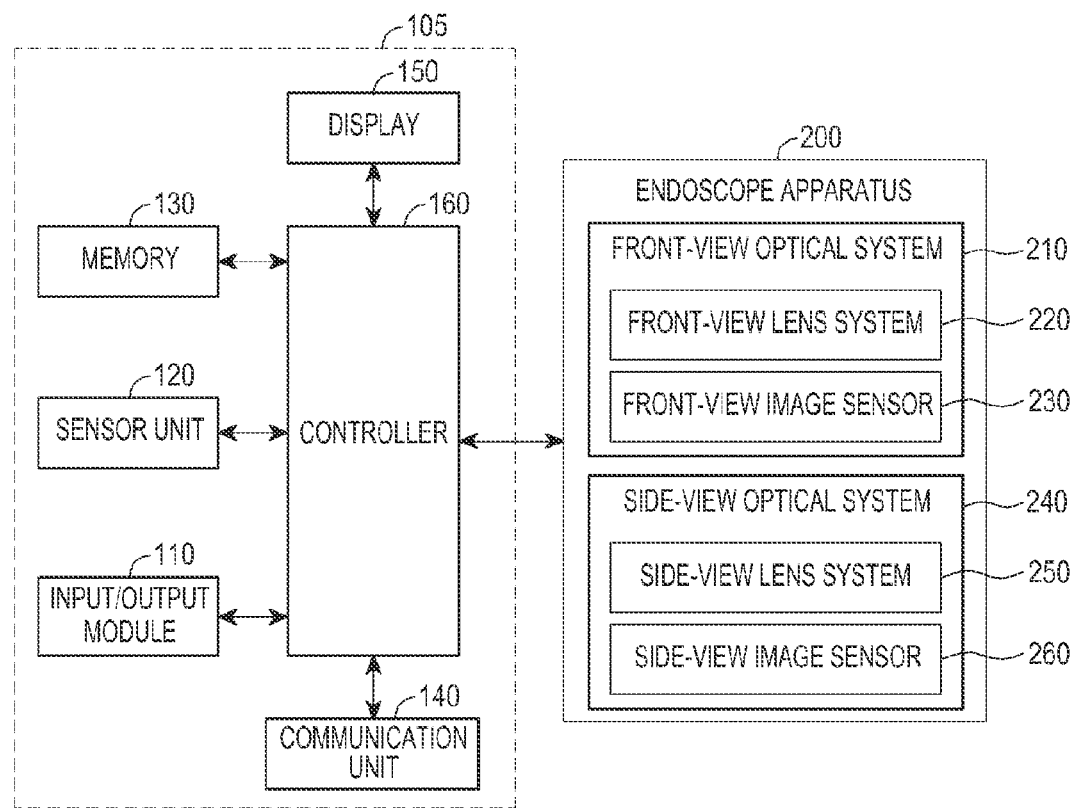
FIG. 2 is a block diagram illustrating a structure of an endoscope system according to an embodiment of the present invention.

FIG. 2 is a diagram illustrating a structure of an endoscope system according to an embodiment of the present invention.

Referring to FIG. 2, an endoscope system 100 may be a combination of a portable or non-portable computing device 105 and an endoscope apparatus 200. The computing device 105 may be a laptop Personal Computer (PC), a tablet PC, or a desk PC. The computing device 105 may also be implemented with a pocket-size portable mobile terminal having a wireless communication function.

The endoscope system 100 may perform operations by communicating or cooperating with an external electronic device. For example, the endoscope system 100 may transmit an image captured by the endoscope apparatus 200 to the external electronic device through a network. The endoscope system 100 may operate under control of the external electronic device, and control by the external electronic device may be implemented in various ways. The network may include, but not limited to, at least one of a Local Area Network (LAN), a Wireless Local Area Network (WLAN), a Wide Area Network (WAN), and a Small Area Network (SAN). The endoscope system 100 may also be directly connected with the external electronic device.

The endoscope system 100 including the computing device 105, may include an input/output module 110, a sensor unit 120, a memory 130, a communication unit 140, a display 150, and a controller 160, and the endoscope apparatus 200.

The input/output module 110 may include a speaker, a microphone, a keyboard, and a connector to receive a user input or provide information to a user. As an additional example of the input/output module 110, a cursor control such as, but not limited to, a mouse, a trackball, a joystick, or cursor direction keys may be provided to control information communication with the controller 160 and cursor movement on the display 150.

The speaker outputs sound corresponding to various signals (for example, a wireless signal, a broadcast signal, a digital audio file, a digital video file, a captured picture, or the like) to the outside of the endoscope system 100 under control of the controller 160. The speaker outputs sound corresponding to a function executed by the endoscope system 100. A single or multiple speakers may be formed in a proper position or positions of the endoscope system 100.

The microphone receives voice or sound and generates an electric signal under control of the controller 160.

The keyboard may include a plurality of buttons for receiving user's character inputs.

The connector may be used as an interface for connecting the endoscope system 100 with a server, an external electronic device, or a power source (not illustrated). Data stored in the memory 130 of the endoscope system 100 may be transmitted to the external electronic device or data may be received from the external electronic device, through a wired cable connected to the connector under control of the controller 160. The endoscope system 100 may receive power or charge a battery from the power source (not illustrated) through a wired cable connected to the connector.

The sensor unit 120 may include at least one sensor for detecting a state (position, azimuth, movement, or the like) or a surrounding environment state of the endoscope system 100 or the computing device 105. Some of the sensors may be disposed in the endoscope apparatus 200. For example, the sensor unit 120 may include a proximity sensor for detecting the user's proximity to the computing device 105 or the endoscope system 100, a motion/orientation sensor for detecting a motion of the computing device 105 or the endoscope apparatus 200 (for example, rotation, acceleration, deceleration, vibration, or the like, of the endoscope system 100), an illumination sensor for detecting ambient illumination, a temperature sensor for measuring an ambient temperature, and so forth. The motion/orientation sensor may include at least one of an acceleration sensor, a gravity sensor, a geomagnetic sensor, a gyro sensor, a shock sensor, a Global Positioning System (GPS) module, and a compass sensor. The sensor unit 120 detects a state of the computing device 105 or the endoscope apparatus 200, and generates and transmits a signal corresponding to the detected state to the controller 160. For example, the GPS sensor may receive electric waves from a plurality of GPS satellites around the earth's orbit and may calculate the position of the endoscope system 100 by using a time of arrival from the GPS satellite to the endoscope system 100. The compass sensor calculates a posture or azimuth of the computing device 105 or the endoscope apparatus 200.

The communication unit 140 is provided for direct connection with a server or an external electronic device, or connection over a network, and may be a wired or wireless communication unit. The communication unit 140 transmits data from the controller 160, the memory 130, and the endoscope apparatus 200 by wire or in a wireless manner, or receives data from an external communication line or over the air in to deliver the data to the controller 160 or store the data in the memory 130.

The communication unit 140 may include at least one of a mobile communication module, a wireless Local Area Network (LAN) module, and a short-range communication module, depending on its functionality. The communication unit 140 may further include at least one of, but is not limited to, a Digital Multimedia Broadcasting (DMB) module, an Integrated Services Digital Network (ISDN) card, a modem, a LAN card, an infrared module, a Bluetooth port, and a Zigbee module.

The mobile communication module enables the endoscope system 100 to communicate with an electronic device through a mobile communication network by using one or more antennas under control of the controller 160. The mobile communication module transmits/receives a radio signal for data exchange such as voice communication, video communication, a Short Messaging Service (SMS), or a Multimedia Messaging Service (MMS) or one-way transmission or reception with a cellular phone, a smart phone, a tablet PC, or another device, which has a phone number or a network address.

The WLAN module may be connected to the Internet under control of the controller 160 in a place where a wireless Access Point is installed. The WLAN module supports a WLAN standard (IEEE802.11x) of the Institute of Electrical and Electronics Engineers (IEEE). The short-range communication module may wirelessly perform short-range communication between the endoscope system 100 and an external electronic device under control of the controller 160. The short-range communication may include Bluetooth®, Infrared Data Association (IrDA), or the like.

The display 150 displays an image input from the controller 160 on a screen. The display 150 may include a Liquid Crystal Display (LCD), an Organic Light Emitting Diode (OLED), an LED, a touch screen, or the like. In the following description, a touch screen including a display unit for displaying an image on a screen and a touch panel for detecting a contact by a user input means is used for the display 150.

The display 150 displays an image corresponding to control of the controller 160, and upon touch of a user input means such as a finger or a stylus pen on the surface thereof, generates a key touch interrupt and outputs user input information including input coordinates and an input state to the controller 160 under control of the controller 160.

The display 150 may provide a Graphic User Interface (GUI) corresponding to various services (for example, call, data transmission, broadcasting, picture/video capturing, endoscopy, and so forth) to the user. The display 150 outputs user input information corresponding to at least one touch input to the GUI to the controller 160. The display 150 receives at least one touch through a user's body (for example, a finger) or a touch-possible input device (for example, a stylus pen). The display 150 receives continuous movement of one of the at least one touch. The display 150 transmits user input information corresponding to the received continuous movement of the touch to the controller 160.

In the present invention, the touch may be a contactless touch (for example, when the display 150 and the user's body or the touch-possible input device are spaced apart from each other) as well as a contact between the display 150 and the user's body or the touch-possible input device. The display 150 may be of, for example, a capacitive type.

The memory 130 stores machine executable code including applications of various functions such as endoscopy, video communication, games, and the like, images for providing a GUI related to the applications, user information, documents, databases related to mapping tables of users and endoscopy information, background images (a menu screen, a standby screen, and so forth) or operation programs for driving the endoscope system 100, and endoscopic images captured by the endoscope apparatus 200. The memory 130 is a machine (for example, a computer, a cellular phone, or the like)-readable medium and the term "machine-readable medium" may be defined a medium for providing data to a machine to allow the machine to execute a particular function. The machine-readable medium may be a storage medium. The memory 130 may include a non-volatile medium and a volatile medium. Such a medium needs to be of a tangible type so that commands delivered to the medium can be detected by a physical tool which reads the commands with the machine.

The machine-readable medium may include, but not limited to, at least one of a floppy disk, a flexible disk, a hard disk, a magnetic tape, a Compact Disc Read-Only Memory (CD-ROM), an optical disk, a punch card, a paper tape, a Random Access Memory (RAM), a Programmable Read-Only Memory (PROM), an Erasable PROM (EPROM), and a flash EPROM.

The controller 160 executes an application corresponding to user input information, and the application performs a program operation corresponding to the user input information. The user input may be made through a keyboard, the display 150, or the like. The controller 160 may include a bus for information communication and a processor connected with the bus for information processing. The controller 160 may include a second memory (for example, a RAM) connected with the bus to store information needed by the processor. The second memory may be used to store temporary information needed by the processor. The controller 160 may further include a ROM connected with the bus to store static information required by the processor. The controller 160 controls the overall operation of the endoscope system 100 as a central processing unit.

The endoscope apparatus 200 includes a front-view or front-view-observation optical system 210 for capturing an object situated in front of the endoscope apparatus 200 and a side-view or side-view observation optical system 240 for capturing an object situated at a side of the endoscope apparatus 200.

The front-view optical system 210 may include a front-view lens system 220 that forms a front-view optical image of an object by converging light incident from the front of the endoscope apparatus 200 and a front-view image sensor 230 that converts front-view light (that is, the front-view optical image) input (or captured) through the front-view lens system 220 into an electric front-view image signal or data and outputs the front-view image signal or data to the controller 160.

The side-view optical system 240 may include a side-view lens system 250 that forms a side-view optical image of the object by converging side-view light incident from a side of the endoscope apparatus 200 and a side-view image sensor 260 that converts side-view light (that is, the side-view optical image) input (or captured) through the side-view lens system 250 into electric side-view image data and outputs the electric side-view image data to the controller 160.

The front-view optical system 210 and the side-view optical system 240 may further include flashes for illuminating the object. The endoscope apparatus 200 may further include a laser apparatus or tool for removing or curing a lesion.

Although one side-view optical system is illustrated in this example, two or more side-view optical systems may be used as described below.

Herein, terms that express uses for respective components may be substituted by ordinal numbers and for example, the front-view optical system, the front-view lens system, and the front-view image sensor may be replaced with a first optical system, a first lens system, and a first image sensor. Also, the first side-view optical system, the first side-view lens system, and the first side-view image sensor may be replaced with a second optical system, a second lens system, and a second image sensor. The second side-view optical system, the second side-view lens system, and the second side-view image sensor may be substituted by a third optical system, a third lens system, and a third image sensor.

Each of the lens systems 220 and 250 forms an image of an object by converging light incident from outside. Each of the lens systems 220 and 250 includes at least one lens, which may be a convex or aspheric lens. Each of the lens systems 220 and 250 is symmetric with respect to a corresponding optical axis passing through the center thereof, and the optical axis is defined as a central axis. Each of the image sensors 230 and 260 detects an optical image formed by external light incident through a corresponding lens system as electric image data. Each of the image sensors 230 and 260 may include a plurality of pixel units arranged in an M×N matrix form, and each pixel unit may include a photodiode and a plurality of transistors. Each pixel unit accumulates an electric charge generated by the incident light, and a voltage corresponding to the accumulated electric charge indicates an illumination of the incident light. When a still image or a video image is processed, image data output from each of the image sensors 230 and 260 includes a group of voltages (that is, pixel values) output from pixel units, and the image data represents one frame (that is, a still image). A frame includes M×N pixels. Each of the image sensors 230 and 260 may include a Charge-Coupled Device (CCD) image sensor, a Complementary Metal-Oxide Semiconductor (CMOS) image sensor, or the like.

The controller 160 processes image data input from the endoscope apparatus 200 or image data stored in the memory 130 in units of frames, and outputs image data converted to fit to screen characteristics (size, quality, resolution, and so forth) of the display 150.

Figure 3:
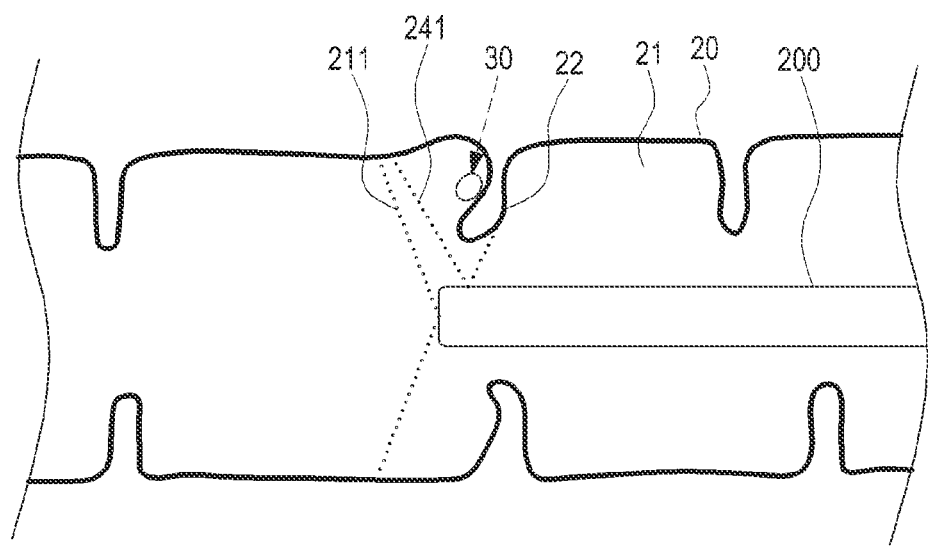
FIG. 3 is a diagram describing the field of view of an endoscope apparatus according to an embodiment of the present invention.

FIG. 3 is a diagram describing the field of view of the endoscope apparatus 200.

Referring to FIG. 3, the endoscope apparatus 200 situated in the interior 21 of the large intestine 20 forms an image of an object situated in the front by using the front-view optical system 210, but if a lesion 30 is occluded by a curved portion 22 of the large intestine 20, the lesion 30 is out of a front field of view 211 of the front-view optical system 210 and thus fails to be detected by the front-view optical system 210.

The side-view optical system 240 forms an image of an object situated at a first side of the endoscope apparatus 200 and has a side field of view 241.

As shown in FIG. 3, the lesion 30 occluded by the curved portion 22 is detected by the side-view optical system 240. The front field of view 211 of the front-view optical system 210 and the side field of view 241 of the side-view optical system 240 may overlap with each other at edge portions thereof.

Figure 4:
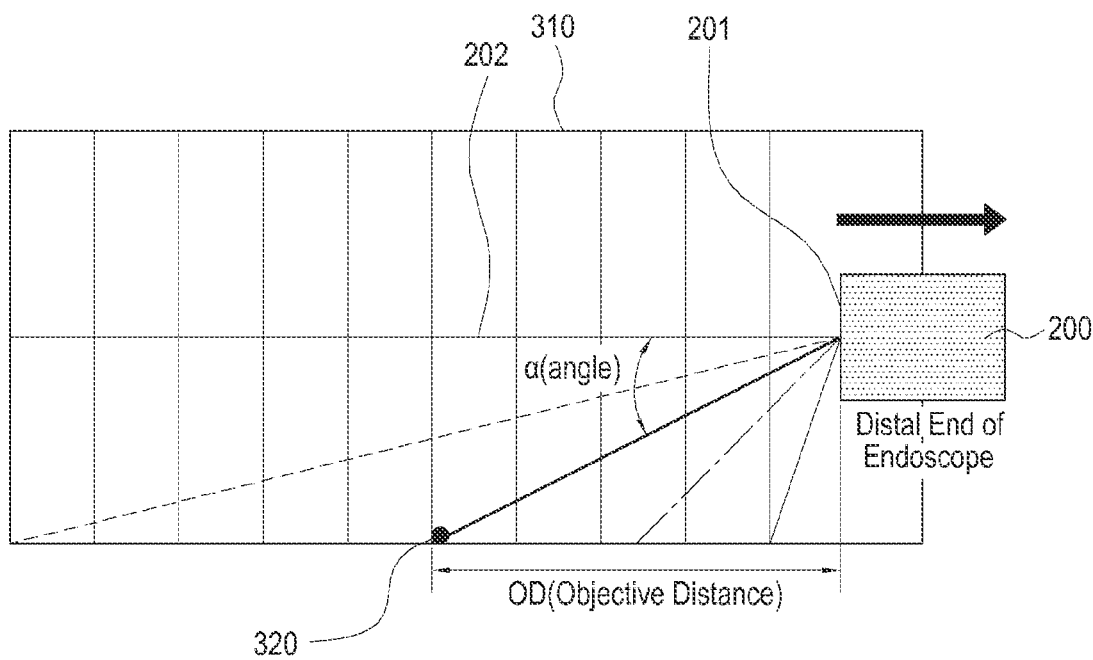
FIGS. 4 and 5 are diagrams describing screening of an interior of a large intestine by using an endoscope apparatus according to an embodiment of the present invention.
Figure 5:
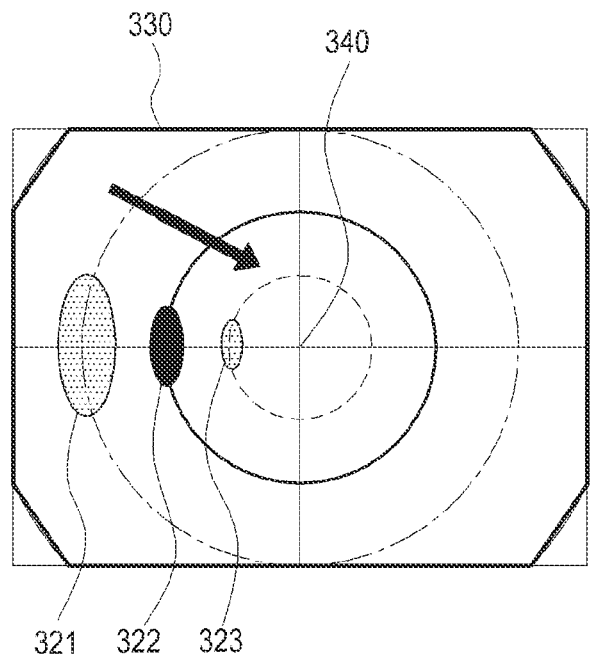

FIGS. 4 and 5 are diagrams describing screening of an interior of a large intestine by using the endoscope apparatus 200 according to the present invention.

In the large intestine, the size or diameter of the large intestine varies with a position along the longitudinal direction of the large intestine or from person to person, but the large intestine may be regarded as having a cylindrical shape having a diameter of about 50 mm on average. Hereinbelow, in FIGS. 4 to 7, the large intestine is regarded as a cylinder having a diameter of about 50 mm.

FIGS. 4 and 5 conceptually describe changes in size and position of a lesion image displayed on the screen of the display 150 when the endoscope apparatus 200 is moved backwards along the longitudinal direction of the large intestine to screen the interior of the large intestine.

FIG. 4 illustrates the endoscope apparatus 200 moved backwards along the longitudinal direction of a large intestine 310 and a lesion 320 generated in an inner side of the large intestine 310. In light of the front-view optical system 210, an objective distance (or an object distance) is defined as a distance between the lesion 320 and a front end 201 of the endoscope apparatus 200 (which is the same as a front end of the front-view optical system 210) along the longitudinal direction of the large intestine 310. An object angle is defined as an angle formed between a segment connecting the center of the front end 201 of the endoscope apparatus 200 with the lesion 320 and an optical axis 202 of the endoscope apparatus 200 (which is the same as an optical system of the front-view optical system 210).

FIG. 5 illustrates changes in size and position of the lesion 320 displayed on a screen 330 of the display 150 as the endoscope apparatus 200 is moved backwards. A lesion image 321 appearing for the first time in an outermost portion of the screen 330 of the display 150 moves toward a center 340 of the screen 330 and is reduced in size (in FIG. 5, 321→322→323), as the endoscope apparatus 200 is moved backward. Thus, it can be seen that the outermost portion of the screen 330 is located closest to the front end 201 of the endoscope apparatus 200.

Figure 6:
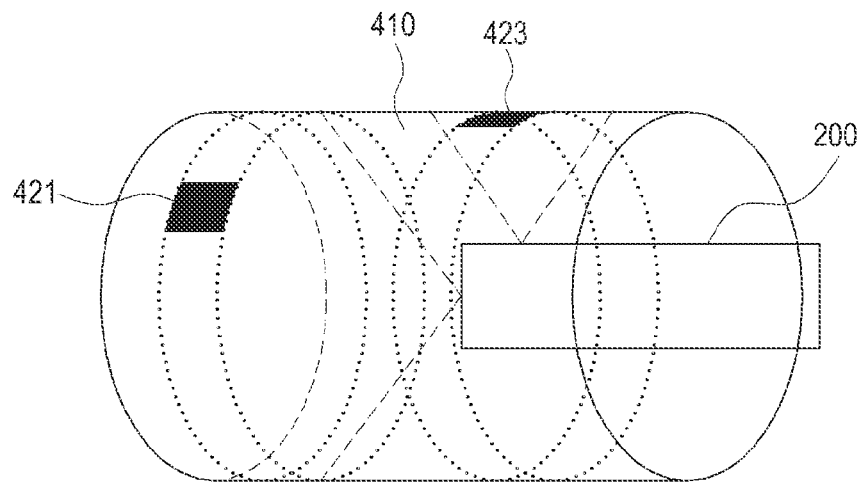
FIGS. 6 and 7 are diagrams describing a position relationship between lesions captured by an endoscope apparatus according to an embodiment of the present invention.
Figure 7:
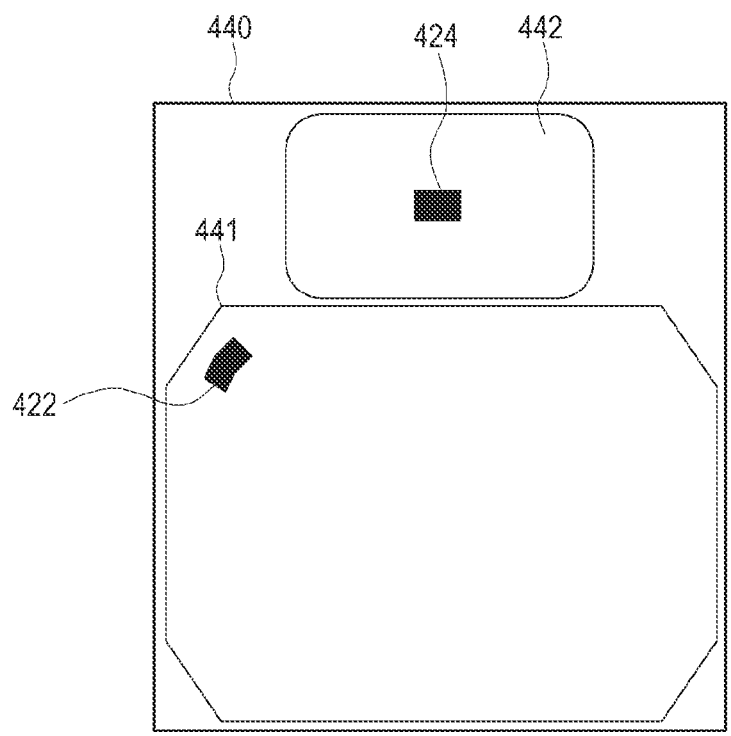

FIGS. 6 and 7 are diagrams describing a position relationship between lesions captured by the endoscope apparatus 200.

In FIG. 6, the endoscope apparatus 200 is located in the center of a large intestine 410, a first lesion 421 is situated in front of the endoscope apparatus 200, and a second lesion 423 is situated at a side of the endoscope apparatus 200.

FIG. 7 shows first and second lesion images 422 and 424 captured by the endoscope apparatus 200 when a center of a front end of the endoscope apparatus 200 is located in the center of the large intestine 410.

FIG. 7 illustrates a screen 440 of the display 150 on which a front-view region 441 displaying an image captured by the front-view optical system 210 and a side-view region 442 displaying an image captured by the side-view optical system 240 are provided. The first lesion image 422 is displayed in an edge portion of the front-view region 441, and the second lesion image 424 is displayed in a center portion of the side-view region 442.

From the positions of the lesion images 422 and 424, it may be determined that the lesion is situated near the front end of the endoscope apparatus 200.

If a lesion is detected by both the front-view optical system 210 and the side-view optical system 240, the size of a lesion image displayed in the edge portion of the front-view region 441 and the size of a lesion image displayed in of the side-view region 442 may be similar with each other. In this case, it may be determined that the lesion is situated near the front end of the endoscope apparatus 200, and it may be easy to observe one lesion through the front-view region 441 and the side-view region 442. In this state, if the endoscope apparatus 200 is moved backwards, the first lesion image 422 may move from the edge portion to the center portion in the front-view region 441 and the second lesion image 424 may move from the center portion to the edge portion.

On the other hand, if the size of the first lesion image 422 shown in the edge portion of the front-view region 441 and the size of the second lesion image 424 displayed in the side-view region 442 are different from each other, it may be difficult to determine that the lesion images 422 and 424 correspond to the same lesion and it may also be difficult to observe one lesion through the front-view region 441 and the side-view region 442.

In terms of a resolution of a lens system that enables identification of a lesion and a magnifying power of the lens system that affects the size of a lesion image, the front-view lens system 220 and the side-view lens system 250 may have different characteristics from each other. If the magnifying power of the front-view lens system 220 and the magnifying power of the side-view lens system 250 are quite different from each other, the lesion image captured by a low-resolution and low-magnifying power optical system looks as if it is out of focus, such that a difference or discrepancy occurs between a front-view image and a side-view image for the same lesion.

Before providing a detailed description of characteristics of the present invention associated with resolution, the resolution will be defined first as below based on a front-view optical system.

Figures 8A, 8B:
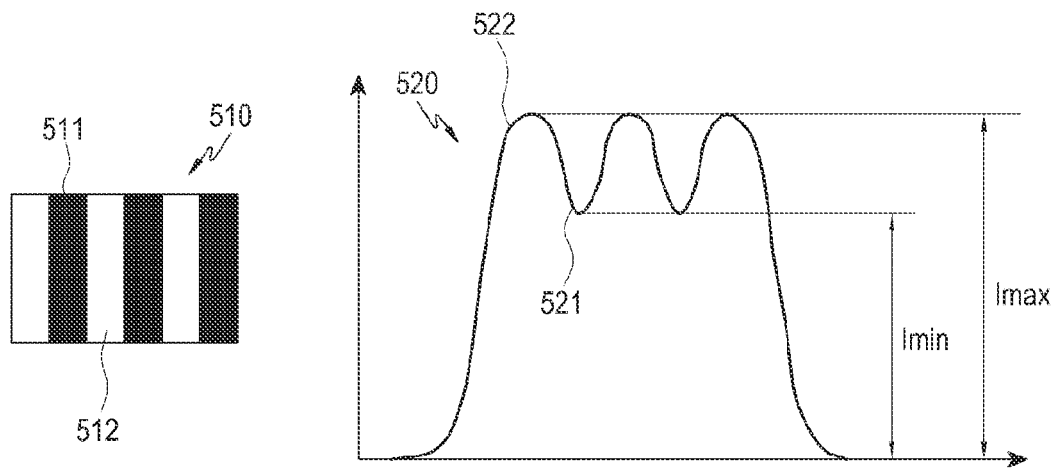
FIGS. 8A and 8B are diagrams for describing a resolution of a front-view or front-view-observation optical system according to an exemplary embodiment of the present invention.

FIGS. 8A and 8B are diagrams describing a resolution of a front-view optical system according to an embodiment of the present invention.

FIG. 8A illustrates an object 510 having alternating black lines 511 and white lines 512 that have the same width as one another. The black lines 511 may be substituted by dots that are spaced apart from one another.

FIG. 8B is a graph showing a luminance distribution 520 of an image of the object 510 captured by the front-view optical system 210, in which a horizontal axis indicates a widthwise position of the object 510 and a vertical axis indicates a luminance. In the luminance distribution 520, white luminance parts 522 corresponding to the white lines 512 and black luminance parts 521 corresponding to the black lines 511 alternate one by one. Let a luminance maximum value of the white luminance parts 522 be "Imax" and a luminance minimum value of the black luminance parts 521 be "Imin", then a contrast C of the white luminance parts 522 and the black luminance parts 521 is defined by Equation (1) as follows:

$$C = \frac{I\max - I\min}{I\max + I\min} \quad (1)$$

In a particular object distance (that is, a distance between the object 510 and the front end of the endoscope apparatus 200), when the contrast C is 9%, the reciprocal of a width of a pair of the black and white lines 511 and 512 is defined as a resolution of the front-view optical system 210 in the object distance. In this case, the white line 512 and the black line 511 have the same width as each other, such that the width of the black-white-line pair is equal to the double of a width of each line. For example, if the width of the black-white-line pair is 0.1 mm for the contrast C of 9% in a particular object distance, then the resolution of the front-view optical system 210 in the particular object distance is the reciprocal of the width of the black-white-line pair, that is, 10 lp/mm, where lp denotes a unit expressing the number of line pairs.

A limit resolution R in the center of the front-view image sensor 230 of the front-view optical system 210 is defined by Equation (2) as follows:

$$R = Req \cdot \frac{EFL}{X + Ff}, \quad (2)$$

where Req denotes an equivalent resolution indicating a minimum width of a black-white-line pair that may be recognized on an image surface (that is, a top surface or a light receiving surface of the front-view image sensor 230), X denotes an object distance (that is, a distance between the object and the front end of the endoscope apparatus 200), Ff denotes a front focal length of the front-view optical system 210, and EFL denotes an effective focal length of the front-view optical system 210. Generally, a focal length refers to an effective focal length. The focal length is the distance over which initially collimated light (or rays) is brought to a focus. The front focal length is the distance from the front (or object-side) focal point of the optical system to the vertex of the object-side first optical surface of the optical system.

The equivalent resolution may be expressed as a product of a pixel pitch p of the front-view image sensor 230 times a circuit characteristic coefficient k indicating circuit characteristics of a controller for processing front-view image data output from the front-view image sensor 230, or the equivalent resolution may also be approximated by Equation (3) as follows:

$$Req \approx \frac{1}{s\sqrt{\left(1 \cdot \frac{845\lambda F}{s}\right)^2 + 1}}, \quad (3)$$

where s denotes a pixel size, λ denotes a predetermined average wavelength with respect to light incident to the front-view optical system 210 (for example, an average wavelength of d rays (587.6 nm), e rays (546.1 nm), and f rays (486.1 nm)), and F denotes an F-number of the front-view optical system 210. In this case, the pixel size may be less than or equal to the pixel pitch p.

Suppose a first limit resolution and a second limit resolution of the front-view optical system 210 with respect to object distances of 50 mm and 30 mm to be R1 (lp/mm) and R2 (lp/mm) and a third limit resolution of the side-view optical system 240 with respect to the object distance of 30 mm to be R3 (lp/mm). Also, suppose for object close observation of the side-view optical system 240, a minimum object distance corresponding to a minimum limit resolution R4 (lp/mm) of the side-view optical system 240 is d1 (mm) and a limit resolution of the front-view optical system 210 in the object distance d1 is R5 (lp/mm).

When the interior of a large intestine is screened to detect a lesion of the large intestine, the center of the front end of the endoscope apparatus 200 is disposed in the center of the large intestine and in this case, the object distance of the side-view optical system 240 may be about 15 mm-30 mm. Thus, if the third limit resolution R3 of the side-view optical system 240 with respect to a lesion situated 30 mm from the front end of the side-view optical system 240 (that is, with respect to an object distance of 30 mm) is much larger than the second limit resolution R2 of the front-view optical system 210 with respect to the object distance of 30 mm, magnifying power and resolution of the side-view optical system 240 are higher than those of the front-view optical system 210. In this case, for the same lesion, a lesion image displayed in a side-view region looks larger than a lesion image displayed in a front-view region, and the resolution of the front-view optical system 210 is low, resulting in a discrepancy between the two lesion images.

To maintain performance of the side-view optical system 240, the size of the side-view lens system 250 and the size of the side-view image sensor 260 increase, such that the diameter of the front end portion of the endoscope apparatus 200 may also increase. Moreover, if the third limit resolution R3 is even smaller than the first limit resolution R1 of the front-view optical system 210 for the object distance of 50 mm, the resolution and magnifying power of the side-view optical system 240 become smaller than those of the front-view optical system 210. Also in this case, for the same lesion, a difference occurs between the lesion image displayed in the side-view region and the lesion image displayed in the front-view region. Furthermore, due to low magnifying power and resolution of the side-view optical system 240, a rate of missed lesions occluded by a curved portion of the large intestine with the side-view optical system 240 may increase.

If the minimum limit resolution R4 of the side-view optical system 240 is smaller than the limit resolution R5 of the front-view optical system 210 in d1, it is difficult to observe a lesion in a magnified form by using the low-resolution side-view optical system 240, and thus, it is necessary to observe the lesion in a magnified form by using the front-view optical system 210. Observation of the lesion in a magnified form using the front-view optical system 210 may be accompanied by additional manipulation by bending the front end portion of the endoscope apparatus 200. Hence, to make it easy to observe the lesion in a magnified form and observe the lesion minutely without unnecessary manipulation, R4 needs to be larger than R5 to allow the lesion to be observed in a magnified form without the unnecessary step of bending the front end portion of the endoscope apparatus 200, by using the side-view optical system 240.

Figure 9:
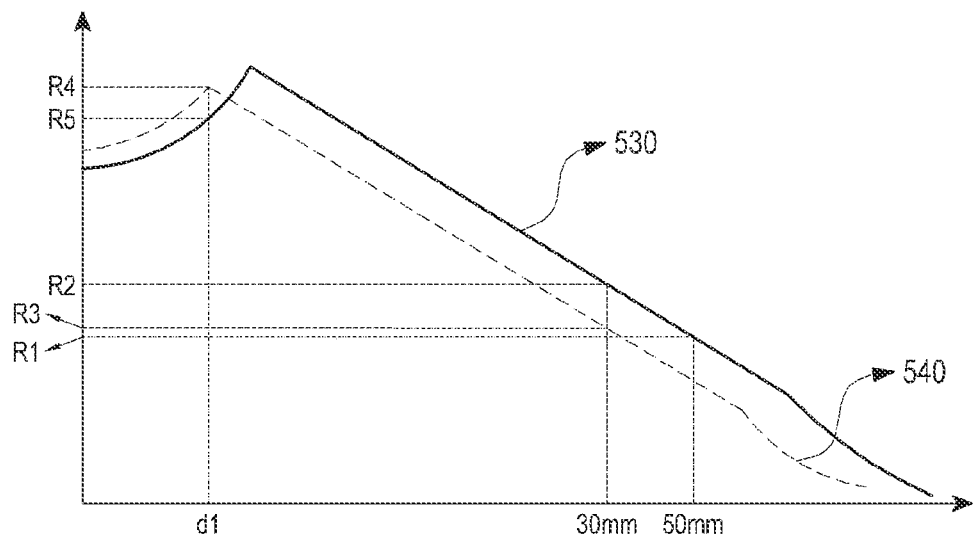
FIGS. 9 and 10 are graphs showing changes in limit resolutions of a front-view optical system and a side-view optical system with respect to changes in an object's distance according to an embodiment of the present invention.
Figure 10:
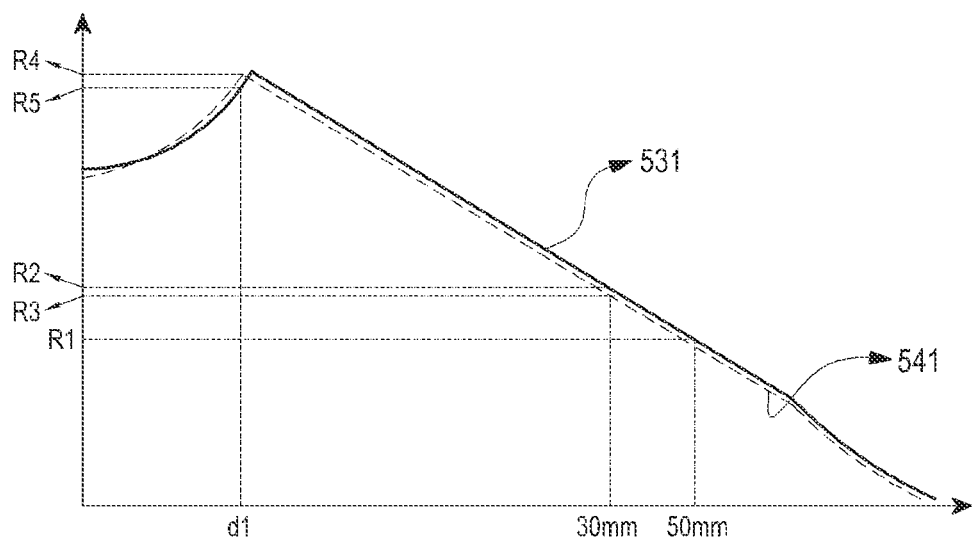

FIGS. 9 and 10 are graphs showing changes in limit resolutions of the front-view optical system 210 and the side-view optical system 240 with respect to changes in object distance. In FIGS. 9 and 10, a horizontal axis indicates an object distance and a vertical axis indicates a limit resolution.

In FIG. 9, limit resolutions of the front-view optical system 210 and the side-view optical system 240 differ greatly with respect to changes in object distance. In FIG. 10, the limit resolutions of the front-view optical system 210 and the side-view optical system 240 differ little with respect to changes in object distance.

Referring to FIG. 9, a limit resolution graph 530 of the front-view optical system 210 and a limit resolution graph 540 of the side-view optical system 240 are spaced apart from each other. It may be also seen from FIG. 9 that the third limit resolution R3 is smaller than the second limit resolution R2 of the front-view optical system 210 and is larger than the first limit resolution R1 of the front-view optical system 210. Also, the minimum limit resolution R4 of the side-view optical system 240 is larger than the limit resolution R5 of the front-view optical system 210 in the object distance d1.

Referring to FIG. 10, a limit resolution graph 531 of the front-view optical system 210 and a limit resolution graph 541 of the side-view optical system 240 almost coincide with each other. It may also be seen from FIG. 10 that the third limit resolution R3 is larger than the first limit resolution R1 of the front-view optical system 210 and is smaller than the second limit resolution R2 of the front-view optical system 210, and the minimum limit resolution R4 of the side-view optical system 240 is larger than the limit resolution R5 of the front-view optical system 210 in the object distance d1.

The endoscope apparatus 200 according to the present invention may satisfy the following conditions of Equations (4), (5), (6) and (7):

$$350 < \frac{IH1}{P1} < 800, \quad (4)$$

$$0.95 < \frac{IH1}{EFL1} < 1.3, \quad (5)$$

$$250 < \frac{IH2}{P2} < 600, \quad (6)$$

$$0.7 < \frac{IH2}{EFL2} < 1.2, \quad (7)$$

wherein IH1 denotes a maximum image height on the image surface of the front-view image sensor 230, IH2 denotes a maximum image height of the side-view image sensor 260, P1 denotes a pixel pitch of the front-view image sensor 230, P2 denotes a pixel pitch of the side-view image sensor 260, EFL1 denotes a focal length of the front-view optical system 210, and EFL2 denotes a focal length of the side-view optical system 240.

Figure 11A:
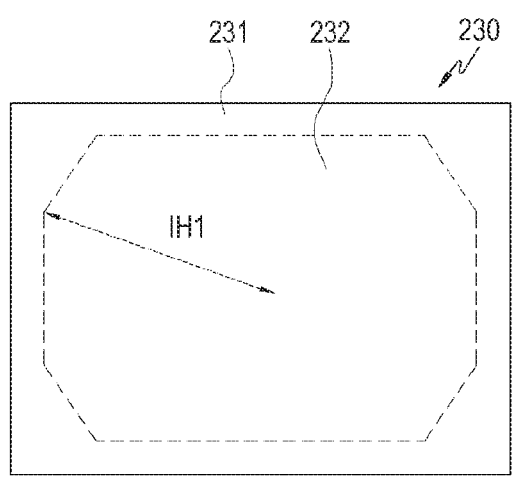
FIGS. 11A and 11B are diagrams describing a maximum height according to an embodiment of the present invention.
Figure 11B:
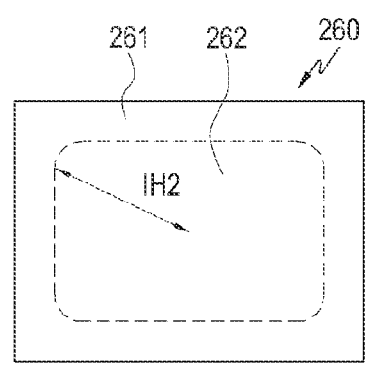

FIGS. 11A and 11B are diagrams describing a maximum image height.

FIG. 11A shows the front-view image sensor 230 including an effective region 232 displayed on the display 150 on the surface of the front-view image sensor 230 on which pixels are arranged, that is, on an image surface 231 of the front-view image sensor 230. The effective region 232 corresponds to the front-view region (441 of FIG. 7) and a distance from the center of the effective region 232 to the outermost portion of the effective region 232 corresponds to a maximum image height IH1.

FIG. 11B shows the side-view image sensor 260 including an effective region 262 displayed on the display 150 on the surface of the side-view image sensor 260 on which pixels are arranged, that is, on an image surface 261 of the side-view image sensor 260. The effective region 262 corresponds to the side-view region (442 of FIG. 7) and a distance from the center of the effective region 262 to the outermost portion of the effective region 262 corresponds to a maximum image height IH2.

In the endoscope apparatus 200 according to the present invention, the third limit resolution R3 of the side-view optical system 240 may be smaller than the second limit resolution R2 of the front-view optical system 210 and may be larger than the first limit resolution R1 of the front-view optical system 210.

In the endoscope apparatus 200 according to the present invention, the minimum limit resolution R4 of the side-view optical system 240 may be larger than the limit resolution R5 of the front-view optical system 210 in the object distance d1.

If the front-view optical system 210 satisfies a condition of Equation (4) and fails to satisfy a lower limit of a condition of Equation (5), the field of view of the front-view optical system 210 is reduced, reducing a lesion detection rate.

If the front-view optical system 210 satisfies the condition of Equation (4) and fails to satisfy an upper limit of a condition of Equation (5), the field of view of the front-view optical system 210 is increased, increasing an outer diameter of an object-side first lens of the front-view optical system 210 and thus increasing a diameter of the front end portion of the endoscope apparatus 200.

If the front-view optical system 210 satisfies the condition of Equation (5) and fails to satisfy a lower limit of the condition of Equation (4), a curvature of a lens of the front-view lens system 220 is increased, such that an outer diameter of the lens is sharply reduced, making it difficult to process the lens and increasing a processing error, thus degrading the performance of the front-view optical system 210 and reducing a detection rate with respect to a lesion. The curvature may be defined to be the reciprocal of the radius of the lens.

If the front-view optical system 210 satisfies the condition of Equation (5) and fails to satisfy an upper limit of the condition of Equation (4), the focal length and outer diameter of the front-view optical system 210 increase, making it difficult to reduce the diameter of the front end portion of the endoscope apparatus 200.

If the side-view optical system 240 satisfies a condition of Equation (6) and fails to satisfy a lower limit of a condition of Equation (7), the field of view of the side-view optical system 240 is reduced, reducing a detection rate with respect to the lesion situated in the curved portion of the large intestine.

If the side-view optical system 240 satisfies the condition of Equation (6) and fails to satisfy an upper limit of the condition of Equation (7), the field of view of the side-view optical system 240 is increased, but the outer diameter of the object-side first lens of the side-view optical system 240 is also increased, lengthening the front end portion of the endoscope apparatus 200 along a longitudinal direction of the front end portion and thus increasing a radius of gyration of the front end portion of the endoscope apparatus 200.

Also, with increase in the outer diameters of lenses of the side-view optical system 240, the diameter of the front end portion of the endoscope apparatus 200 increases.

If the side-view optical system 240 satisfies a condition of Equation (7) and fails to satisfy a lower limit of the condition of Equation (6), the resolution of the side-view optical system 240 is reduced, making it difficult to observe the lesion in a magnified form and thus requiring an unnecessary step of bending the front end portion of the endoscope apparatus 200 for observation of the lesion in a magnified form with the front-view optical system 210.

If the side-view optical system 240 satisfies the condition of Equation (7) and fails to satisfy an upper limit of the condition of Equation (6), the size of the side-view image sensor 260 increases, and in particular, when a plurality of side-view optical systems 240 are disposed on the front end portion of the endoscope apparatus 200, the diameter of the front end portion of the endoscope apparatus 200 increases.

FIGS. 12 to 15 are diagrams describing a structure of an endoscope apparatus 600 according to a first embodiment (Embodiment 1) of the present invention.

Figure 12:
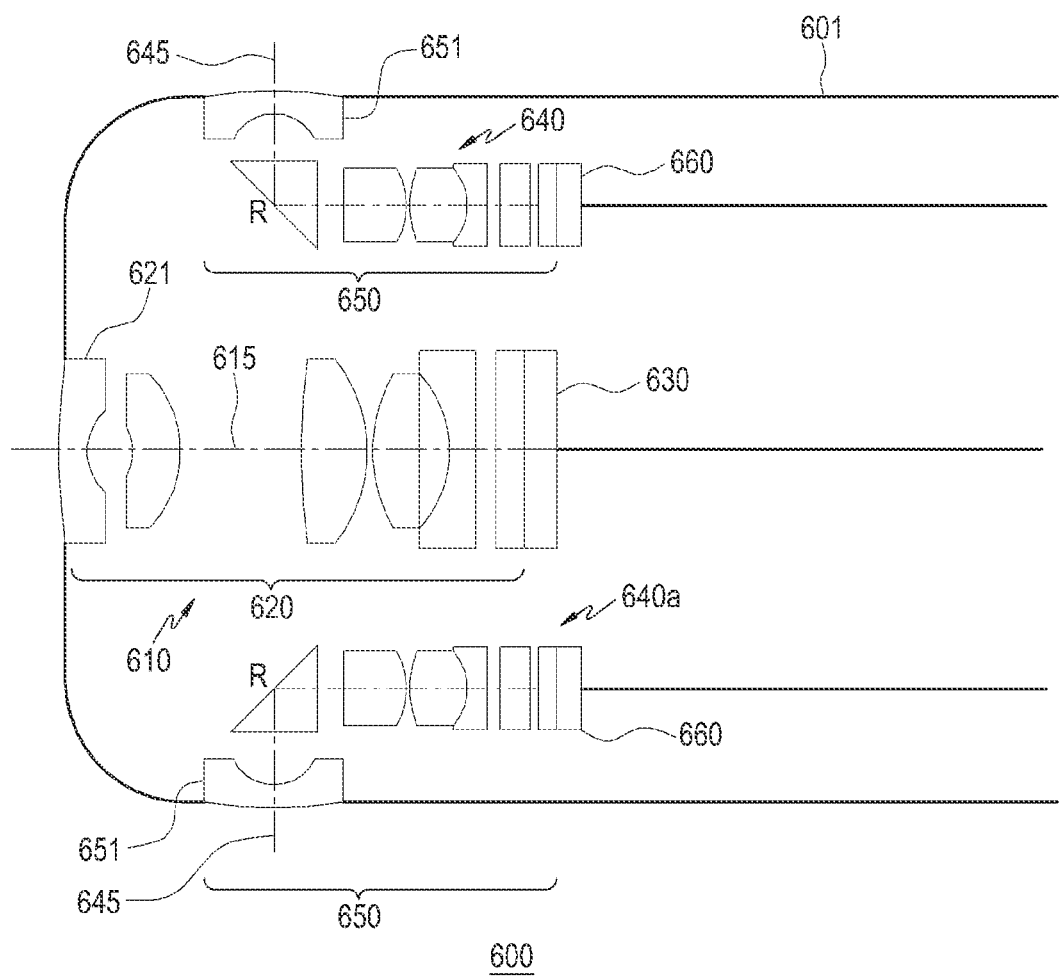
FIGS. 12 to 16 are diagrams describing an endoscope apparatus according to a first embodiment of the present invention.
Figure 13:
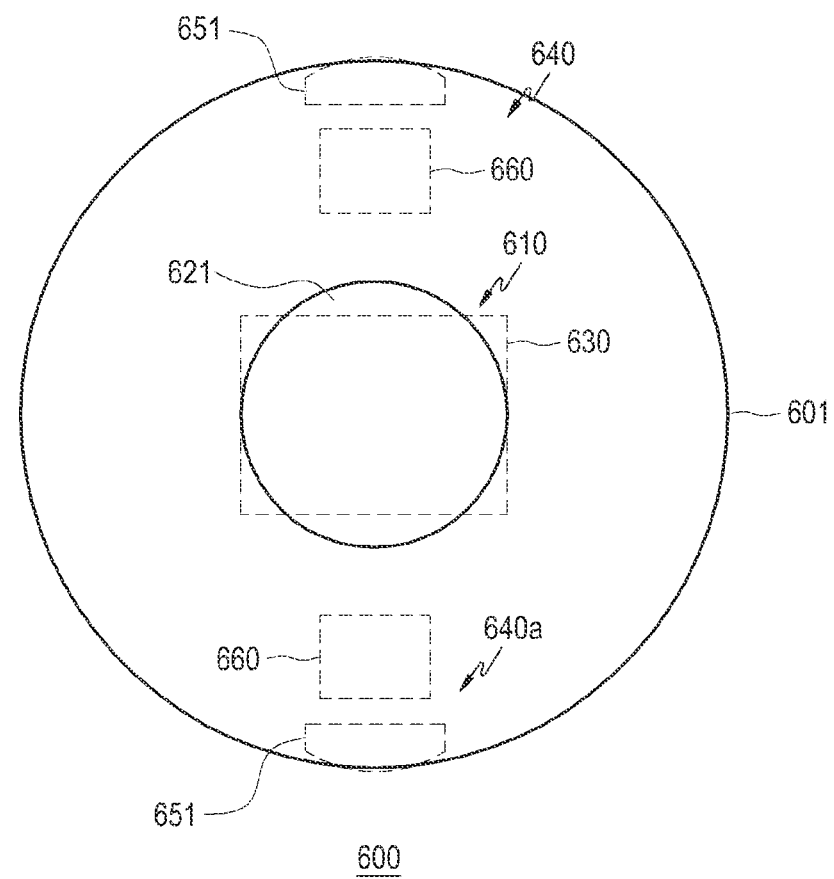

FIG. 12 is a cross-sectional view illustrating a front end portion of the endoscope apparatus 600. FIG. 13 is a diagram illustrating a front surface of the endoscope apparatus 600. FIG. 13 illustrates each image sensor and a first lens of each lens system, in which a first lens 621 of a front-view lens system 620 is exposed to a front surface of a housing 601 and a first lens 651 of each side-view lens system 650 is exposed to a lateral surface of the housing 601.

The endoscope apparatus 600 may include the housing 601 in a circular tubular form having a closed front surface, a front-view optical system 610 that is located in a center portion of the housing 601 and includes the front-view lens system 620 and the front-view image sensor 630, and first and second side-view optical systems 640 and 640a located at both sides of the front-view optical system 610 in the housing 601. The first and second side-view optical systems 640 and 640a have the same structure as each other, and each of them may include the side-view lens system 650 and a side-view image sensor 660. Image data detected by each image sensor is delivered to a controller (not shown) through a corresponding wire. The front-view optical system 610 is aligned along a first optical axis 615 that is parallel to a longitudinal direction of the endoscope apparatus 600, and each of the side-view optical systems 640 and 640a is aligned along a second optical axis 645 bent by a reflecting surface R of a prism.

Each image sensor may be a color image sensor in which a color filter is disposed for each pixel. The front-view image sensor 630 may have an aspect ratio of 4:3. In this case, a viewing angle of a short-side direction of the front-view image sensor 630 is smaller than that of a long-side direction of the front-view image sensor 630. Referring to FIG. 13, the long-side direction is a horizontal direction and the short-side direction is a vertical direction. Thus, it is preferable to dispose the first and second side-view optical systems 640 and 640a at both sides of the front-view optical system 610 along the short-side direction of the front-view image sensor 630.

Figure 14:
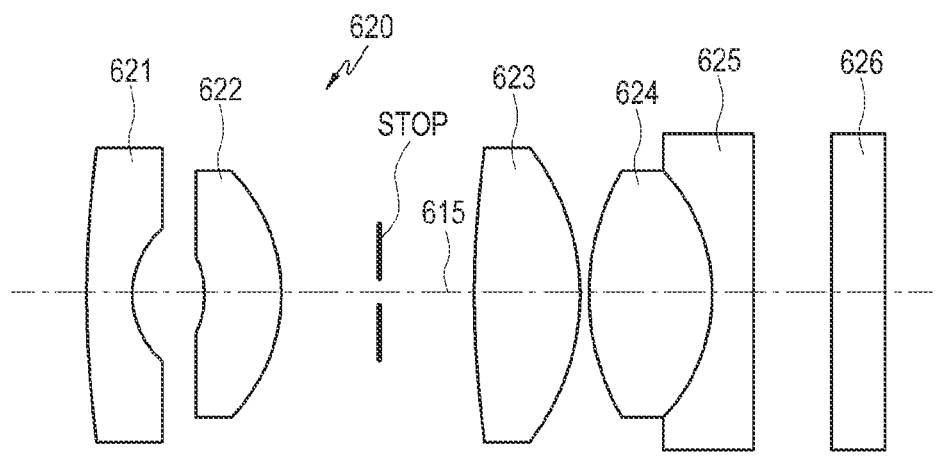

FIG. 14 is a diagram illustrating the front-view lens system 620 according to the first embodiment of the present invention.

Referring to FIG. 14, the front-view lens system 620 includes a first lens 621, a second lens 622, a third lens 623, a fourth lens 624, a fifth lens 625, and a second filter 626 that are arranged on the first optical axis 615. Generally, an optical axis refers to an axis in which an optical device has no optical change in spite of rotation around the axis. When an optical device is arranged on an optical axis, it means that the center of curvature of the optical device is located on the optical axis or a symmetric point (that is, a center of symmetry) or a center point of the optical device is located on the optical axis.

The front-view lens system 620 forms an optical image of an object situated within a viewing angle of the front-view lens system 620 on an image surface of the front-view image sensor 630, and the front-view image sensor 630 then converts the optical image into electric image data.

In the following description of the present invention, a first filter is used to block laser light output from a laser device for removing or curing a lesion and the first filter may block light of 1064 nm of an Yttrium Aluminum Garnet (YAG) laser or light of 810 nm of a semiconductor laser. A second filter is used to block Infrared (IR) rays and a filter for such a purpose may be generally referred to as an IR cut-off filter. The second filter may be an IR-absorbing filter or IR-interfering filter. A third filter is used to block a laser beam together with the YAG laser, and may cut off light of 1064 nm of the YAG laser or light of 810 nm of the semiconductor laser. The second filter is directly stacked on the image surface of the image sensor, and an image-side optical surface of the second filter coincides with the image surface of the image sensor. The image surface of the image sensor refers to the surface of pixel units. In the examples of the present invention, to facilitate understanding, filters are indicated by ordinal numbers corresponding to usages, and the ordinal numbers are limited to examples of the present invention and may be selected at random.

Table 1 provided below shows numeric data of optical devices of the front-view lens system 620. Table 1 shows a surface number i, a radius of curvature of an $i^{th}$ optical surface $S_i$, R, a thickness or air interval of the $i^{th}$ optical surface (or a distance from the $i^{th}$ optical surface to an $(i+1)^{th}$ optical surface), D, a refractive index $n_d$ in a d-line (587.5618 nm) of the $i^{th}$ optical surface, and an Abbe's number of the $i^{th}$ optical surface in the d-line, $v_d$. The unit of a radius of curvature and the unit of a thickness are millimeters (mm). The optical surface number i is sequentially added in a direction from the object toward an image surface. For example, in the first lens 621, the first optical surface may be referred to as an object-side optical surface and the second optical surface may be referred to as an image-side optical surface. An iris STOP having a circular aperture provided in a center portion thereof is disposed between the second lens 622 and the third lens 623, and the iris STOP controls the amount of light incident to a lens positioned behind the iris STOP through the circular aperture. An image-side optical surface of the second filter 626 coincides with an image surface of the front-view image sensor 630 and IMAGE denotes the image surface.

In the front-view lens system 620, EFL1=0.858, IH1=0.900, P1=1.40 μm, 2ω=135°, F/#=7.2, and D0=7.8 mm (best focus). 2ω denotes a viewing angle, F/# denotes an F-number, and D0 denotes an object distance with respect to an image representing best focus.

TABLE 1

| Surface No. | R | D | $n_d$ | $v_d$ | Remarks |
|---|---|---|---|---|---|
| 1 | 18.200 | 0.500 | 1.80610 | 40.90 | First Lens |
| 2 | 1.100 | 0.890 | | | |
| 3 | -2.580 | 0.980 | 1.84666 | 23.80 | Second Lens |
| 4 | -2.150 | 0.900 | | | |

TABLE 1-continued

| Surface No. | R | D | $n_d$ | $v_d$ | Remarks |
|---|---|---|---|---|---|
| 5 | INFINITY | 1.550 | | | Iris (STOP) |
| 6 | 31.500 | 1.240 | 1.83481 | 47.73 | Third Lens |
| 7 | -2.860 | 0.100 | | | |
| 8 | 3.100 | 1.570 | 1.78800 | 47.35 | Fourth and Fifth |
| 9 | -2.100 | 0.470 | 2.15400 | 17.20 | Lenses |
| 10 | INFINITY | 1.020 | | | |
| 11 | INFINITY | 0.600 | 1.51680 | 64.20 | Second Filter |
| IMAGE | INFINITY | 0.000 | | | |

In Table 1, in terms of the direction from the object to the image surface, the first lens 621 has first and second optical surfaces which are convex-concave, and the fourth lens 624 has eighth and ninth optical surfaces which are bi-convex. The fourth and fifth lenses 624 and 625 are double cemented lenses, and in terms of the direction from the object to the image surface, the fifth lens 625 has ninth and tenth optical surfaces which are concave-planar. If an optical surface is planar, the radius of curvature, R, goes to infinity and the refractive index $n_d$ of the air is 1. In the current example, optical surfaces all are spherical, but they may also be aspherical. In this case, the radius of curvature, R, of the aspheric surface is expressed as a value measured in the center (or the vertex) of the aspheric surface.

The fifth lens 625 including the tenth optical surface may function as the first filter (IR filter).

The second filter 626 has an object-side eleventh optical surface and an image surface which are bi-planar.

Figure 15:
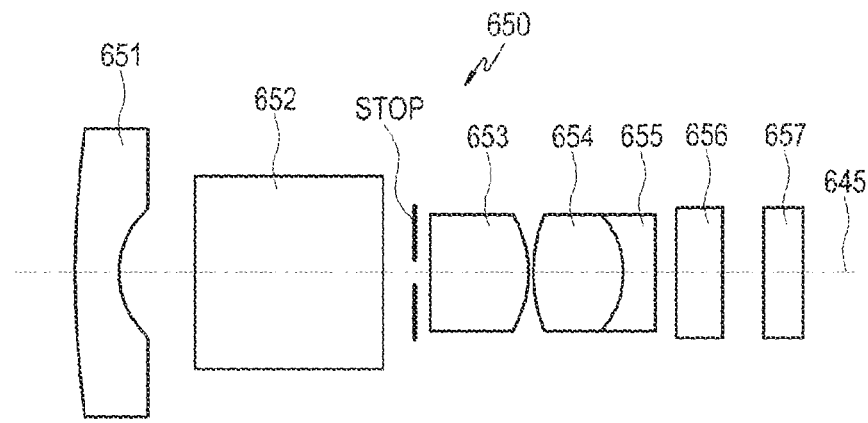

FIG. 15 is a diagram illustrating the side-view lens system 650 according to the first embodiment of the present invention, in which the second optical axis 645 bent in FIG. 12 is unfolded into a straight line. The following description will be made based on the side-view lens system 650 forming the first side-view optical system 640.

Referring to FIG. 15, the side-view lens system 650 includes the first lens 651, a second lens 652, a third lens 653, a fourth lens 654, a fifth lens 655, a first filter 656, and a second filter 657.

The side-view lens system 650 forms an optical image of an object situated within the viewing angle of the side-view lens system 650 on an image surface of the side-view image sensor 660, and the side-view image sensor then converts the optical image into electric image data.

Table 2 provided below shows numeric data of optical devices of the side-view lens system 620. The iris STOP having a circular aperture provided in a center portion thereof is disposed between the second lens 652 and the third lens 653. The iris STOP controls the amount of light incident to a lens located behind the iris STOP through the circular aperture. A image-side optical surface of the second filter 657 coincides with an image surface of the side-view image sensor 660 and IMAGE denotes the image surface.

In the side-view lens system 650, EFL2=0.615, IH2=0.607, P2=1.75 μm, 2ω=140°, F/#=7.0, and D0=8.0 mm (best focus).

TABLE 2

| Surface No. | R | D | nd | vd | Remarks |
|---|---|---|---|---|---|
| 1 | 12.761 | 0.400 | 1.88300 | 40.80 | First Lens |
| 2 | 0.850 | 0.962 | | | |
| 3 | INFINITY | 1.700 | 1.90366 | 31.32 | Second Lens |
| 4 | INFINITY | 0.420 | | | |
| 5 | INFINITY | 0.100 | | | Iris (STOP) |
| 6 | INFINITY | 1.190 | 1.51680 | 64.20 | Third Lens |

TABLE 2-continued

| Surface No. | R | D | nd | vd | Remarks |
|---|---|---|---|---|---|
| 7 | −1.625 | 0.100 | | | |
| 8 | 2.016 | 1.100 | 1.80420 | 46.50 | Fourth and Fifth |
| 9 | −1.209 | 0.400 | 1.92286 | 20.88 | Lenses |
| 10 | INFINITY | 0.265 | | | |
| 11 | INFINITY | 0.600 | 1.51800 | 74.60 | First Filter |
| 12 | INFINITY | 0.598 | | | |
| 13 | INFINITY | 0.455 | 1.51680 | 64.20 | Second Filter |
| IMAGE | INFINITY | 0.000 | | | |

In Table 2, the first lens 651 has first and second optical surfaces which are convex-concave, and the fourth lens 654 has eighth and ninth optical surfaces which are bi-convex. The second lens 652 is a triangular prism and has an object-side third optical surface and an image-side fourth optical surface that are bi-planar, and also has a reflecting surface between the third optical surface and the fourth optical surface to bend the optical axis. The fourth lens 654 and the fifth lens 655 are double cemented lenses, and the fifth lens 655 has ninth and tenth optical surfaces that are concave-planar.

The first filter 656 has an object-side eleventh optical surface and an image-side twelfth optical surface that are bi-planar. The second filter 657 has an object-side thirteenth optical surface and an image surface which are bi-planar.

Figure 16:
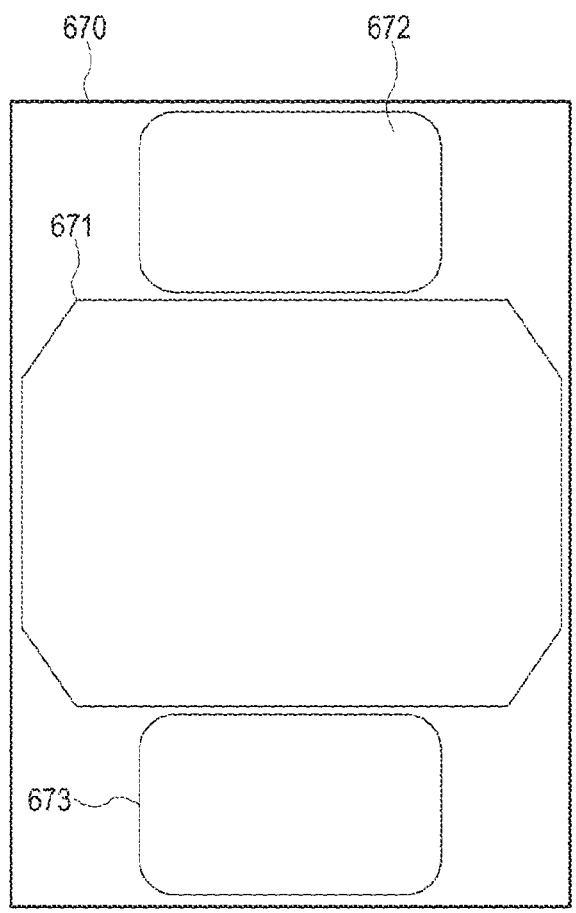

FIG. 16 illustrates a screen 670 of the display 150 according to the first embodiment of the present invention. On the screen 670 of the display 150, a front-view region 671 displaying an image captured by the front-view optical system 610 and first and second side-view regions 672 and 673 displaying images captured by the first and second side-view optical systems 640 and 640a are provided.

Based on the conditions of Equations (4) to (7), the first and second side-view optical systems 640 and 640a may be configured to be smaller than the front-view optical system 610 for similar viewing angles. Moreover, by configuring the first and second side-view optical systems 640 and 640a small, the endoscope apparatus 600 may be size-reduced or miniaturized while having a plurality of side-view optical systems disposed in the front end portion of the endoscope apparatus 600. Furthermore, by shortening a focal length to miniaturize the first and second side-view optical systems 640 and 640a, for similar F-numbers, the minimum limit resolution R4 of the side-view optical systems 640 and 640a is set larger than the fifth limit resolution R5 of the front-view optical system 610 in the object distance d1, object magnification (or object close-up) of the first and second side-view optical systems 640 and 640a are possible. Thus, without an additional step of bending the front end portion of the endoscope apparatus 600 to observe a lesion in a magnified form by using the front-view optical system 610, the lesion may be observed in a magnified form by using the first and second side-view optical systems 640 and 640a. In addition, the third limit resolution R3 of the first and second side-view optical systems 640 and 640a is set smaller than the second limit resolution R2 of the front-view optical system 610, such that the resolution and magnifying power of the first and second side-view optical systems 640 and 640a are not very different from the resolution and magnifying power of the front-view optical system 610 in observing the lesion, thus reducing a discrepancy between a front-view image and side-view images.

FIGS. 17 to 20 are diagrams describing a structure of an endoscope apparatus 700 according to a second embodiment (Embodiment 2) of the present invention.

Figure 17:
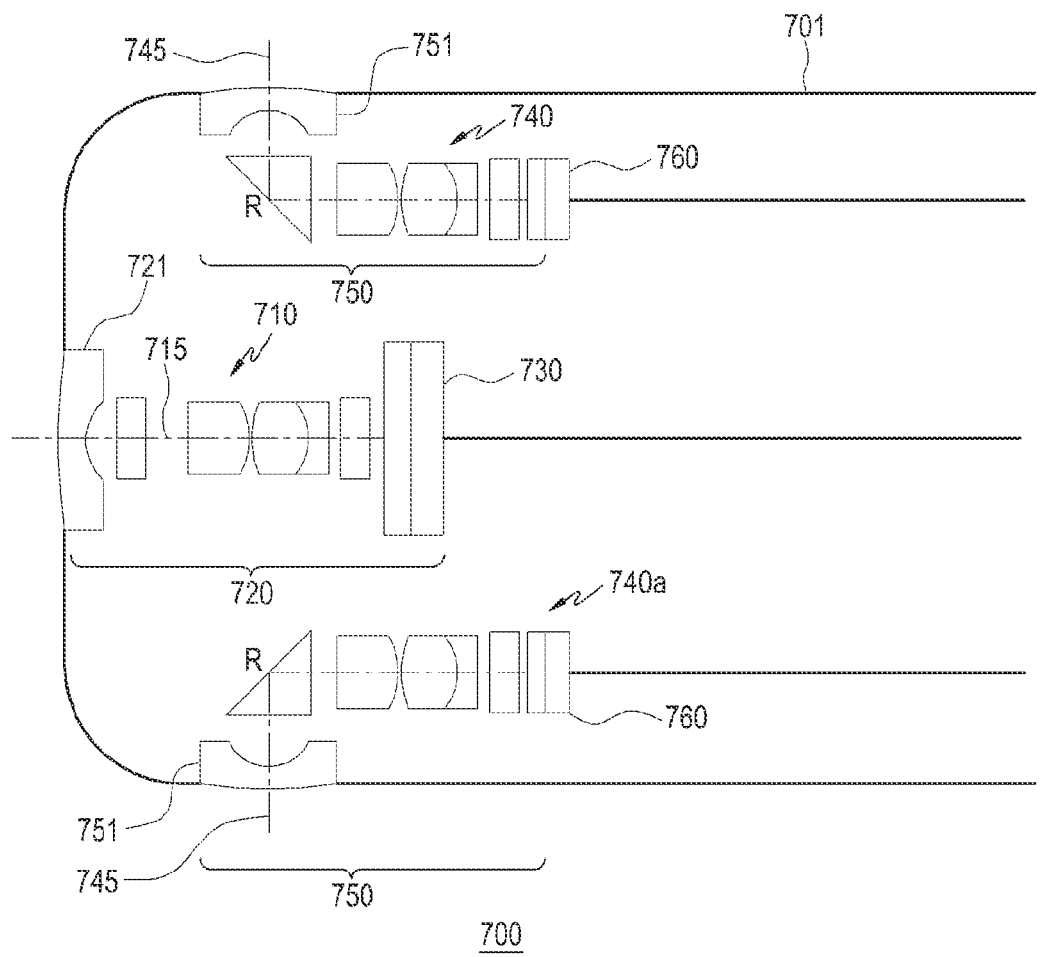
FIGS. 17 to 21 are diagrams describing an endoscope apparatus according to a second embodiment of the present invention.
Figure 18:
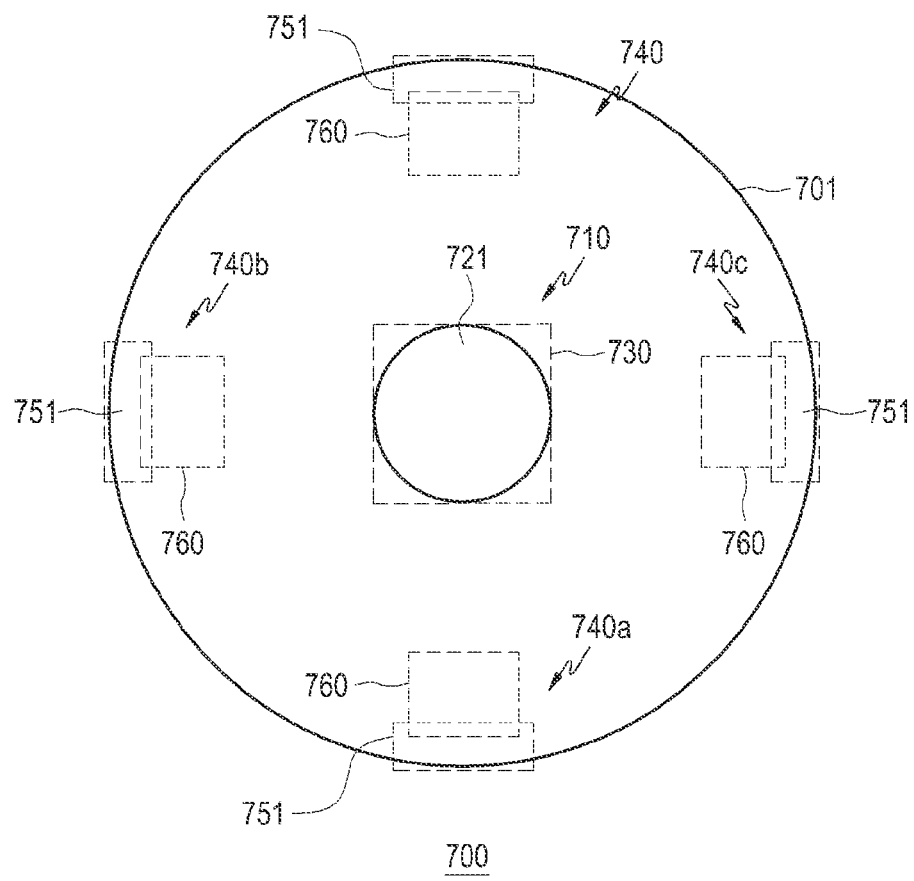

FIG. 17 is a cross-sectional view illustrating a front end portion of the endoscope apparatus 700, and FIG. 18 is a diagram illustrating a front surface of the endoscope apparatus 700. In FIG. 18, each image sensor and a first lens of each lens system are shown, a first lens 721 of a front-view lens system 720 is exposed to a front surface of a housing 701, and a first lens 751 of each side-view lens system 750 is exposed to a lateral surface of the housing 701.

The endoscope apparatus 700 may include a housing 701 in a circular tubular form having a closed front surface, a front-view optical system 710 that is located in a center portion of the housing 701 and includes a front-view lens system 720 and a front-view image sensor 730, and first to fourth side-view optical systems 740, 740a, 740b, and 740c arranged in a cross form along a circumference of the front-view optical system 710 in the housing 701. The first to fourth side-view optical systems 740, 740a, 740b, and 740c have the same structure as one another, and each includes a side-view lens system 750 and a side-view image sensor 760. Image data detected by each image sensor is delivered to a controller (not shown) through a corresponding wire. The front-view optical system 710 is aligned along a first optical axis 715 that is parallel to a longitudinal direction of the endoscope apparatus 700, and each of the side-view optical systems 740, 740a, 740b, and 740c is aligned along a second optical axis 745 bent by a reflecting surface R of a prism.

Each image sensor may be a color image sensor in which a color filter is arranged for each pixel, and the front-view image sensor 730 may have an aspect ratio of 1:1.

Figure 19:
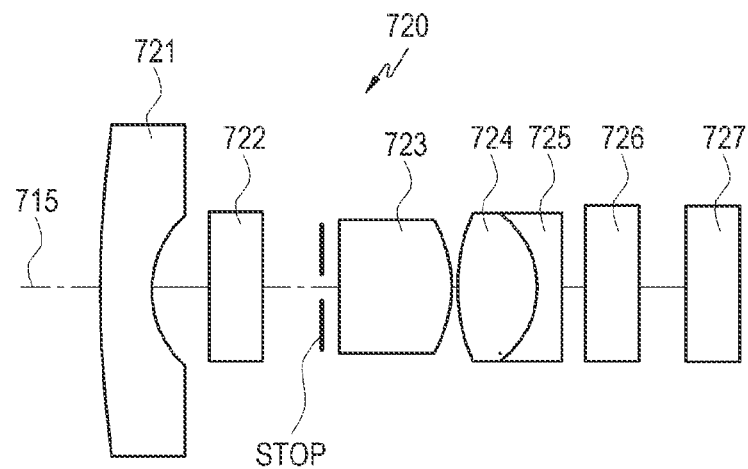

FIG. 19 is a diagram illustrating the front-view lens system 720 according to the second embodiment of the present invention.

Referring to FIG. 19, the front-view lens system 720 includes a first lens 721, a third filter 722, a second lens 723, a third lens 724, a fourth lens 725, a first filter 726, and a second filter 727 that are aligned on the first optical axis 715.

The front-view lens system 720 forms an optical image of an object situated within a viewing angle of the front-view lens system 720 on an image surface of the front-view image sensor 730, and the front-view image sensor 730 converts an optical image into electric image data.

Table 3 provided below shows numeric data of optical devices of the front-view lens system 720. An iris STOP having a circular aperture provided in a center portion thereof is disposed between the third filter 722 and the second lens 723. The iris STOP controls the amount of light incident to a lens located behind the iris STOP through the circular aperture. An image-side optical surface of the second filter 727 coincides with an image surface of the front-view image sensor 730 and IMAGE denotes the image surface.

In the front-view lens system 720, EFL1=0.633, IH1=0.646, P1=1.75 μm, 2ω=140°, F/#=5.2, and D0=8.0 mm (best focus).

TABLE 3

| | R | D | nd | vd | Remarks |
|---|---|---|---|---|---|
| 1 | 15.000 | 0.400 | 1.88300 | 40.80 | First Lens |
| 2 | 0.981 | 0.520 | | | |
| 3 | INFINITY | 0.600 | 1.51680 | 64.20 | Third Filter |
| 4 | INFINITY | 0.845 | | | |
| 5 | INFINITY | 0.100 | | | Iris (STOP) |
| 6 | INFINITY | 1.526 | 1.68958 | 50.83 | Second Lens |
| 7 | −1.496 | 0.120 | | | |
| 8 | 2.472 | 0.995 | 1.80811 | 46.50 | Third and Fourth |

TABLE 3-continued

| | R | D | nd | vd | Remarks |
|---|---|---|---|---|---|
| 9 | −1.100 | 0.235 | 1.90504 | 18.45 | Lenses |
| 10 | −42.401 | 0.100 | | | |
| 11 | INFINITY | 0.600 | 1.51800 | 74.60 | First Filter |
| 12 | INFINITY | 0.550 | | | |
| 13 | INFINITY | 0.455 | 1.51680 | 64.20 | Second Filter |
| IMAGE | INFINITY | 0.000 | | | |

In Table 3, the first lens 721 has first and second optical surfaces that are convex-concave, and the third lens 724 has eighth and ninth optical surfaces that are bi-convex. The third and fourth lenses 724 and 725 are double cemented lenses, and the second lens 723 has sixth and seventh optical surfaces that are planar-convex. The fourth lens 725 has ninth and tenth optical surfaces that are concave-convex. In the current example, the optical surfaces are spherical, but each optical surface may be aspheric.

The third filter 722 has an object-side third optical surface and an image-side fourth optical surface that are bi-planar. The first filter 726 has an object-side eleventh optical surface and an image-side twelfth optical surface that are bi-planar. The second filter 727 has an object-side thirteenth optical surface and an image surface which are bi-planar.

Figure 20:
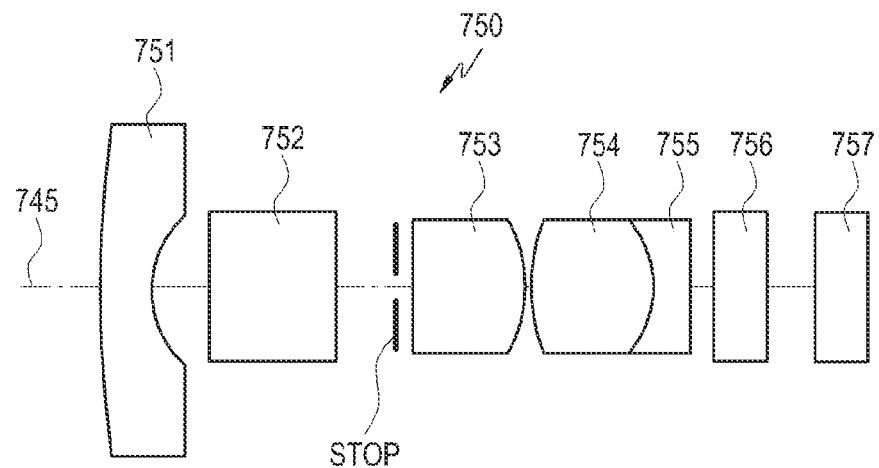

FIG. 20 is a diagram illustrating the side-view lens system 750 according to a second embodiment of the present invention, in which the second optical axis 745 bent in FIG. 17 is unfolded into the straight line. The following description will be made based on the side-view lens system 750 forming the first side-view optical system 740.

The side-view lens system 750 includes the first lens 751, a second lens 752, a third lens 753, a fourth lens 754, a fifth lens 755, a first filter 756, and a second filter 757.

The side-view lens system 750 forms an optical image of an object situated within a viewing angle of the side-view lens system 750 on an image surface of the side-view image sensor 760, and the side-view image sensor 760 converts the optical image into electric image data.

Table 4 provided below shows numeric data of optical devices of the side-view lens system 750. An iris STOP having a circular aperture provided in a center portion thereof is arranged between the second lens 752 and the third lens 753. The iris STOP controls the amount of light incident to a lens positioned behind the iris STOP through the circular aperture. An image-side optical surface of the second filter 757 coincides with an image surface of the side-view image sensor 760 and IMAGE denotes the image surface.

In the side-view lens system 750, EFL2=0.624 IH2=0.448, P2=1.75 μm, 2ω=90°, F/#=6.6, and D0=5.5 mm (best focus).

TABLE 4

| | R | D | nd | vd | Remarks |
|---|---|---|---|---|---|
| 1 | 60.668 | 0.416 | 1.88300 | 40.80 | First Lens |
| 2 | 0.884 | 0.468 | | | |
| 3 | INFINITY | 1.560 | 1.90366 | 31.32 | Second Lens |
| 4 | INFINITY | 0.487 | | | |
| 5 | INFINITY | 0.164 | | | Iris (STOP) |
| 6 | INFINITY | 1.560 | 1.51680 | 64.20 | Third Lens |
| 7 | −1.530 | 0.104 | | | |
| 8 | 2.073 | 1.303 | 1.80420 | 46.50 | Fourth and |
| 9 | −1.248 | 0.416 | 1.92286 | 20.88 | Fifth Lenses |
| 10 | INFINITY | 0.086 | | | |
| 11 | INFINITY | 0.624 | 1.51800 | 74.60 | First Filter |
| 12 | INFINITY | 0.546 | | | |
| 13 | INFINITY | 0.473 | 1.51680 | 64.20 | Second Filter |

TABLE 4-continued

| | R | D | nd | vd | Remarks |
|---|---|---|---|---|---|
| IMAGE | INFINITY | 0.000 | | | |

In Table 4, the first lens 751 is a convex-concave lens, and the fourth lens 754 is a bi-convex lens. The second lens 752 is a triangular prism and has an object-side third optical surface and an image-side fourth optical surface that are bi-planar, and also has a reflecting surface between the third optical surface and the fourth optical surface to bend an optical axis. The fourth lens 754 and the fifth lens 755 are double cemented lenses, and the fifth lens 755 has ninth and tenth optical surfaces that are concave-planar.

The first filter 756 has an object-side eleventh optical surface and an image-side twelfth optical surface that are bi-planar. The second filter 757 has an object-side thirteenth optical surface and an image surface which are bi-planar.

Figure 21:
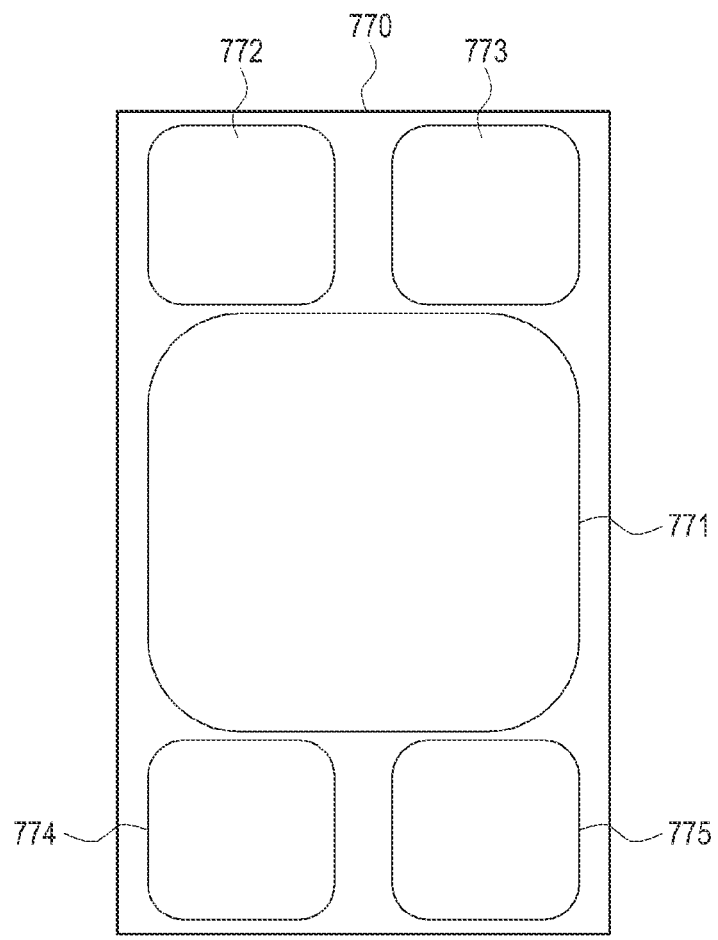

FIG. 21 illustrates a screen 770 of the display 150 according to the second embodiment of the present invention. On the screen 770, a front-view region 771 displaying an image captured by the front-view optical system 710 and first to fourth side-view regions 772, 773, 774, and 775 displaying images captured by the first to fourth side-view optical systems 740, 740a, 740b, and 740c are provided.

Since the conditions of Equations (4) and (7) are satisfied, size increase of the front end portion of the endoscope apparatus 700 may be suppressed in spite of the use of one front-view optical system and four side-view optical systems. Moreover, with the first to fourth side-view optical systems 740, 740a, 740b, and 740c, a curved portion may be thoroughly observed along the circumference of the large intestine, facilitating detection of a lesion in a curved portion of the large intestine. As mentioned previously, the third limit resolution R3 of the side-view optical systems 740, 740a, 740b, and 740c are set smaller than the second limit resolution R2 of the front-view optical system 710, such that the resolution and magnifying power of the first to fourth side-view optical systems 740, 740a, 740b, and 740c are not much different from the resolution and magnifying power of the front-view optical system 710 in observing the lesion, thus reducing a discrepancy between a front-view image and side-view images. Furthermore, the minimum limit resolution R4 of the side-view optical systems 740, 740a, 740b, and 740c is set larger than the fifth limit resolution R5 of the front-view optical system 710 in the object distance d1, such that object magnification of the first to fourth side-view optical systems 740, 740a, 740b, and 740c are possible.

Figure 22:
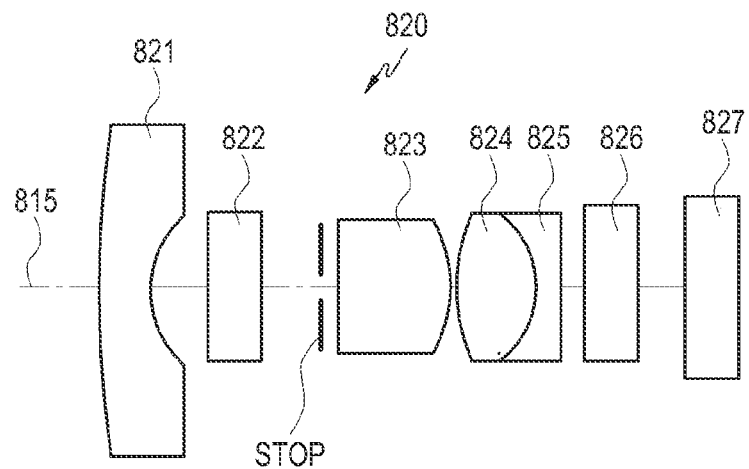
FIGS. 22 and 23 are diagrams describing an endoscope apparatus according to a third embodiment of the present invention.

FIG. 22 is a diagram illustrating a front-view optical system according to a third embodiment (Embodiment 3) of the present invention.

An endoscope apparatus (not illustrated) according to the third embodiment of the present invention may include one front-view optical system and two side-view optical systems like the endoscope apparatus 600 according to the first embodiment of the present invention.

The front-view lens system 820 includes a first lens 821, a third filter 822, a second lens 823, a third lens 824, a fourth lens 825, a first filter 826, and a second filter 827.

The front-view lens system 820 forms an optical image of an object situated within a viewing angle of the front-view lens system 820 on an image surface of a front-view image sensor (not illustrated), and the front-view image sensor converts the optical image into electric image data.

Table 5 provided below shows numeric data of optical devices of the front-view lens system 820. An iris STOP having a circular aperture provided in a center portion thereof is disposed between the third filter 822 and the second lens 823. The iris STOP controls the amount of light incident to a lens located behind the iris STOP through the circular aperture. An image-side optical surface of the second filter 827 coincides with an image surface of the front-view image sensor, and IMAGE denotes the image surface.

In the front-view lens system 820, EFL1=0.800, IH1=0.779, P1=1.40 μm, 2ω=135°, F/#=6.7, and D0=8.0 mm (best focus).

TABLE 5

| | R | D | nd | vd | Remarks |
|---|---|---|---|---|---|
| 1 | 76.136 | 0.400 | 1.88300 | 40.80 | First Lens |
| 2 | 0.981 | 0.520 | | | |
| 3 | INFINITY | 0.600 | 1.51680 | 64.20 | Third Filter |
| 4 | INFINITY | 0.588 | | | |
| 5 | INFINITY | 0.100 | | | Iris (STOP) |
| 6 | INFINITY | 1.646 | 1.64867 | 52.94 | Second Lens |
| 7 | −1.465 | 0.120 | | | |
| 8 | 2.990 | 1.148 | 1.80811 | 46.50 | Third and Fourth |
| 9 | −1.100 | 0.400 | 1.90521 | 21.51 | Lenses |
| 10 | INFINITY | 0.200 | | | |
| 11 | INFINITY | 0.600 | 1.51800 | 74.60 | First Filter |
| 12 | INFINITY | 0.800 | | | |
| 13 | INFINITY | 0.455 | 1.51680 | 64.20 | Second Filter |
| IMAGE | INFINITY | 0.000 | | | |

In Table 5, the first lens 821 has first and second optical surfaces that are convex-concave, and the third lens 824 has eighth and ninth optical surfaces that are bi-convex. The third lens 824 and the fifth lens 825 are double cemented lenses. The second lens 823 has sixth and seventh optical surfaces that are planar-convex. The fourth lens 825 has ninth and tenth optical surfaces that are concave-planar. Although optical surfaces all are spherical in the current example, they may also be aspherical.

The third filter 822 has an object-side third optical surface and an image-side fourth optical surface that are bi-planar. The first filter 826 has an object-side eleventh optical surface and an image-side twelfth optical surface that are bi-planar. The second filter 827 has an object-side thirteenth optical surface and an image surface which are bi-planar.

Figure 23:
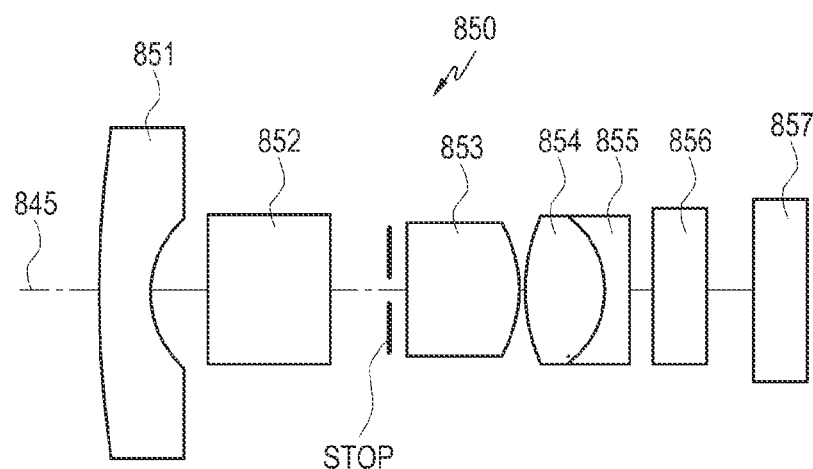

FIG. 23 is a diagram illustrating a side-view lens system 850 according to the third embodiment of the present invention.

Referring to FIG. 23, the side-view lens system 850 may include a first lens 851, a second lens 852, a third lens 853, a fourth lens 854, a fifth lens 855, a first filter 856, and a second filter 857 that are aligned on a second optical axis 845.

The side-view lens system 850 forms an optical image of an object situated within a viewing angle of the side-view lens system 850 on an image surface of a side-view image sensor (not illustrated), and the side-view image sensor converts the optical image into electric image data.

Table 6 provided below shows numeric data of optical devices of the side-view lens system 850. An iris STOP having a circular aperture provided in a center portion thereof is disposed between the second lens 852 and the third lens 850. The iris STOP controls the amount of light incident to a lens located behind the iris STOP through the circuit aperture. An image-side optical surface of the second filter 857 coincides with an image surface of the side-view image sensor, and IMAGE denotes the image surface.

In the side-view lens system 850, EFL2=0.629, IH2=0.616, P2=2.00 μm, 2ω=140°, F/#=8.5, and D0=3.5 mm (best focus).

TABLE 6

| | R | D | nd | vd | Remarks |
|---|---|---|---|---|---|
| 1 | INFINITY | 0.400 | 1.88300 | 40.80 | First Lens |
| 2 | 1.180 | 0.970 | | | |
| 3 | INFINITY | 1.700 | 1.90366 | 31.32 | Second Lens |
| 4 | INFINITY | 0.410 | | | |
| 5 | INFINITY | 0.100 | | | Iris (STOP) |
| 6 | INFINITY | 1.174 | 1.51680 | 64.20 | Third Lens |
| 7 | −1.500 | 0.120 | | | |
| 8 | 2.190 | 0.730 | 1.80420 | 46.50 | Fourth and Fifth |
| 9 | −1.100 | 0.400 | 1.92286 | 20.88 | Lenses |
| 10 | −8.650 | 0.235 | | | |
| 11 | INFINITY | 0.600 | 1.51800 | 74.60 | First Filter |
| 12 | INFINITY | 0.630 | | | |
| 13 | INFINITY | 0.455 | 1.51680 | 64.20 | Second Filter |
| IMAGE | INFINITY | 0.000 | | | |

In Table 6, the first lens 851 has first and second optical surfaces that are planar-concave, and the fourth lens 854 has eighth and ninth optical surfaces that are bi-convex. The second lens 852 is a triangular prism and has an object-side third optical surface and an image-side fourth optical surface that are bi-planar. The second lens 852 also has a reflecting surface that is disposed between the third optical surface and the fourth optical surface to bend an optical axis. The fourth lens 854 and the fifth lens 855 are double cemented lenses, and the fifth lens 855 has ninth and tenth optical surfaces that are concave-convex.

The first filter 856 has an object-side eleventh optical surface and an image-side twelfth optical surface that are bi-planar. The second filter 857 has an object-side thirteenth optical surface and an image surface which are bi-planar.

In the third embodiment of the present invention, the third limit resolution R3 of the side-view optical system approaches the first limit resolution R1 of the front-view optical system, but the resolution and magnifying power of the side-view optical system are not much different from the resolution and magnifying power of the front-view optical system in observing the lesion, thus reducing a discrepancy between a front-view image and a side-view image. Moreover, as R3 approaches R1, a lesion corresponding to a shorter object distance may be observed in a magnified form with the side-view optical system and the magnifying power of the side-view optical system also increases in magnified observation, facilitating detailed magnified observation of the lesion.

FIGS. 24 to 27 are diagrams describing a structure of an endoscope apparatus 900 according to a fourth embodiment of the present invention.

Figure 24:
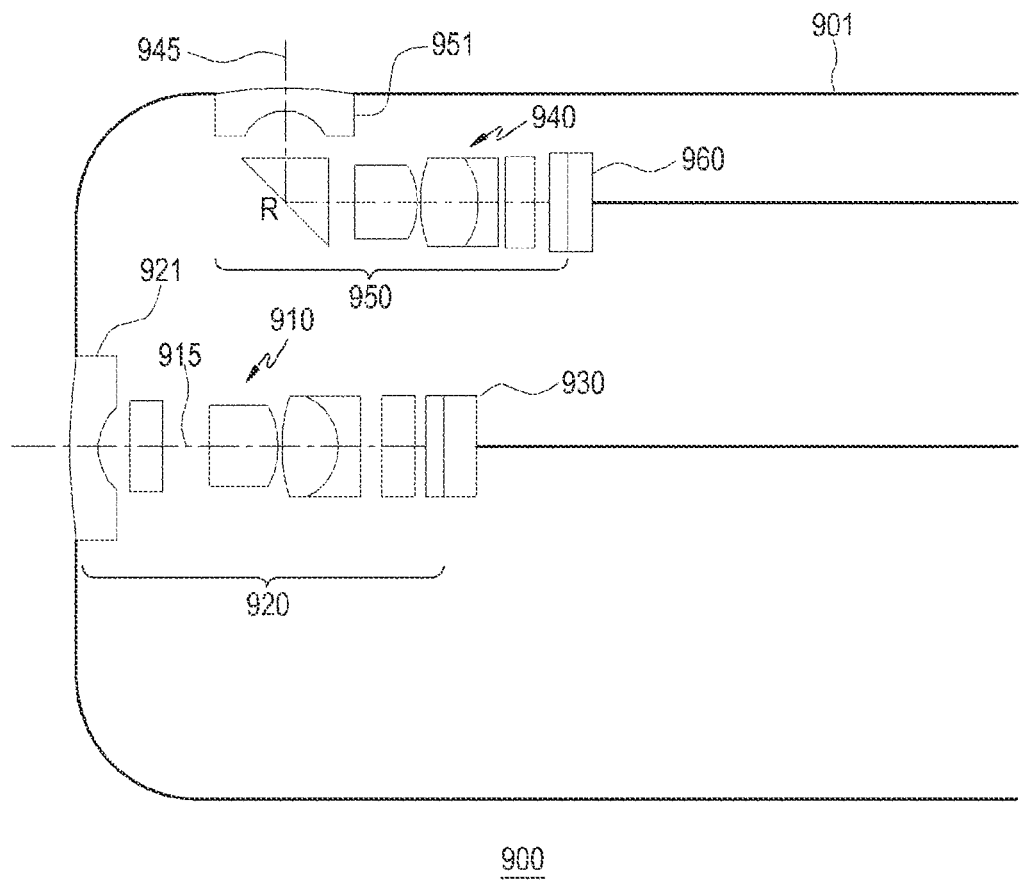
FIGS. 24 to 28 are diagrams describing an endoscope apparatus according to a fourth embodiment of the present invention.
Figure 25:
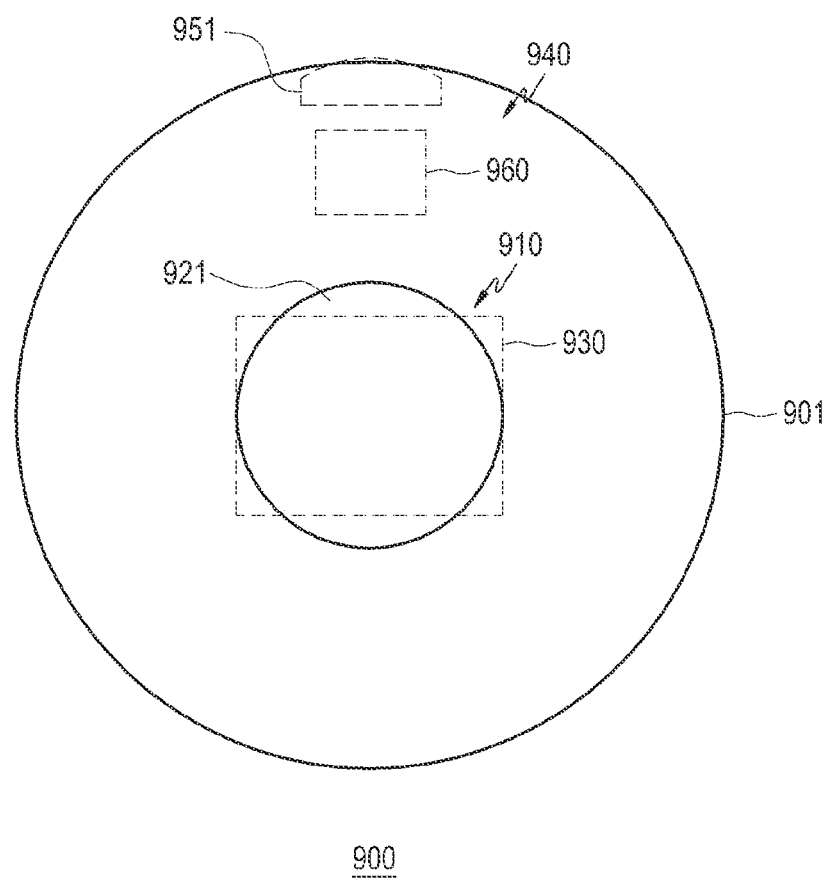

FIG. 24 is a cross-sectional view illustrating a front end portion of the endoscope apparatus 900, and FIG. 25 is a diagram illustrating a front surface of the endoscope apparatus 900. In FIG. 25, each image sensor and a first lens of each lens system are shown, a first lens 921 of a front-view lens system 920 is exposed to a front surface of a housing 901, and a first lens 951 of a side-view lens system 950 is exposed to a lateral surface of the housing 901.

The endoscope apparatus 900 includes the housing 901 in a circular tubular form having a closed front surface, a front-view optical system 910 that is disposed in the center portion of the housing 901 and includes a front-view lens system 920 and a front-view image sensor 930, and a side-view optical system 940 that is disposed at a side of the front-view optical system 910 in the housing 901 and includes a side-view lens system 950 and a side-view image sensor 960. The front-view optical system 910 is aligned along a first optical axis 915 that is parallel to a longitudinal direction of the endoscope apparatus 900, and the side-view optical system 940 is aligned along a second optical axis 945 bent by a reflecting surface R of a prism.

Each image sensor may be a color image sensor in which a color filter is disposed for each pixel, and the front-view image sensor may have an aspect ratio of 4:3. In this case, a viewing angle of a short-side direction of the front-view image sensor 930 is smaller than that of a long-side direction of the front-view image sensor 930. Referring to FIG. 25, the long-side direction is a horizontal direction and the short-side direction is a vertical direction. Thus, it may be preferable to dispose the side-view optical system 940 at a side of the front-view optical system 910 along the short-side direction of the front-view image sensor 930.

Figure 26:
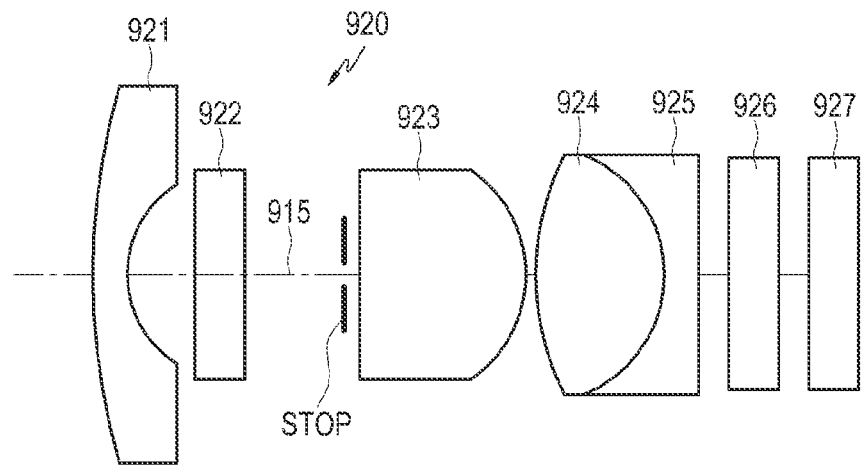

FIG. 26 is a diagram illustrating the front-view lens system 920 according to the fourth embodiment of the present invention.

Referring to FIG. 26, the front-view lens system 920 includes the first lens 921, a third filter 922, a second lens 923, a third lens 924, a fourth lens 925, a first filter 926, and a second filter 927.

The front-view lens system 920 forms an optical image of an object situated within a viewing angle of the front-view lens system 920 on an image surface of the front-view image sensor 930, and the image sensor 930 converts the optical image into electric image data.

Table 7 provided below shows numeric data of optical devices of the front-view lens system 920. An iris STOP having a circular aperture provided in a center portion thereof is disposed between the third filter 922 and the second lens 923. The iris STOP controls the amount of light incident to a lens located behind the iris STOP through the circular aperture. An image-side optical surface of the second filter 927 coincides with an image surface of the front-view image sensor 930, and IMAGE denotes the image surface.

In the front-view lens system 920, EFL1=0.862, IH1=1.042, P1=1.40 μm, 2ω=170°, F/#=6.34, and D0=10 mm (best focus).

TABLE 7

| | R | D | $n_d$ | $v_d$ | Remarks |
|---|---|---|---|---|---|
| 1 | 7.997 | 0.400 | 1.88300 | 40.80 | First Lens |
| 2 | 1.202 | 0.796 | | | |
| 3 | INFINITY | 0.600 | 1.51680 | 64.20 | Third Filter |
| 4 | INFINITY | 1.083 | | | |
| 5 | INFINITY | 0.224 | | | Iris (STOP) |
| 6 | INFINITY | 2.000 | 1.59991 | 63.60 | Second Lens |
| 7 | −1.576 | 0.095 | | | |
| 8 | 2.944 | 1.496 | 1.80796 | 46.53 | Third and Fourth |
| 9 | −1.500 | 0.406 | 1.93029 | 20.97 | Lenses |
| 10 | 42.591 | 0.361 | | | |
| 11 | INFINITY | 0.600 | 1.51800 | 74.60 | First Filter |
| 12 | INFINITY | 0.514 | | | |
| 13 | INFINITY | 0.617 | 1.51680 | 64.20 | Second Filter |
| IMAGE | INFINITY | 0.000 | | | |

In Table 7, the first lens 921 has first and second optical surfaces that are convex-concave, and the third lens 924 has eighth and ninth optical surfaces that are bi-convex. The third lens 924 and the fourth lens 925 are double cemented lenses, and the second lens 923 has sixth and seventh optical surfaces that are planar-convex. The fourth lens 925 has ninth and tenth optical surfaces that are bi-concave. Although optical surfaces all are spherical in the current example, they may also be aspherical.

The third filter 922 has an object-side third optical surface and an image-side fourth optical surface that are bi-planar. The first filter 926 has an object-side eleventh optical surface and an image-side twelfth optical surface that are bi-planar. The second filter 927 has an object-side thirteenth optical surface and an image surface which are bi-planar.

Figure 27:
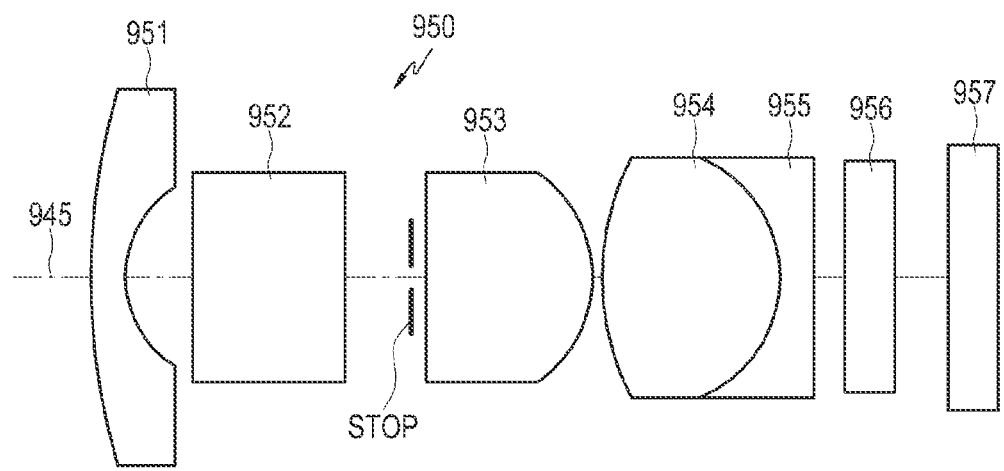

FIG. 27 is a diagram illustrating a side-view lens system 945 according to a fourth embodiment (Embodiment 4) of the present invention, in which the second optical axis 945 bent in FIG. 24 is unfolded into a straight line.

The side-view lens system 950 includes the first lens 951, a second lens 952, a third lens 953, a fourth lens 954, a fifth lens 955, a first filter 956, and a second filter 957.

The side-view lens system 950 forms an optical image of an object situated within a viewing angle of the side-view lens system 950 on an image surface of the side-view image sensor 960, and the side-view image sensor 960 converts the optical image into electric image data.

Table 8 provided below shows numeric data of optical devices of the side-view lens system 950. An iris STOP having a circular aperture provided in a center portion thereof is disposed between the second lens 952 and the third lens 953. The iris STOP controls the amount of light incident to a lens located behind the iris STOP through the circular aperture. An image-side optical surface of the second filter 957 coincides with an image surface of the side-view image sensor 960, and IMAGE denotes the image surface.

In the side-view optical system 940, EFL2=0.786, IH2=0.823, P2=1.40 μm, 2ω=140°, F/#=6.80, and D0=7.0 mm (best focus).

TABLE 8

| | R | D | nd | vd | Remarks |
|---|---|---|---|---|---|
| 1 | 10.799 | 0.403 | 1.88300 | 40.80 | First Lens |
| 2 | 0.981 | 0.468 | | | |
| 3 | INFINITY | 1.560 | 1.90366 | 31.32 | Second Lens |
| 4 | INFINITY | 0.497 | | | |
| 5 | INFINITY | 0.100 | | | Iris (STOP) |
| 6 | INFINITY | 1.486 | 1.51680 | 64.20 | Third Lens |
| 7 | −1.434 | 0.100 | | | |
| 8 | 2.375 | 1.543 | 1.80420 | 46.50 | Fourth and Fifth |
| 9 | −1.149 | 0.416 | 1.92286 | 20.88 | Lenses |
| 10 | INFINITY | 0.086 | | | |
| 11 | INFINITY | 0.624 | 1.51800 | 74.60 | First Filter |
| 12 | INFINITY | 0.608 | | | |
| 13 | INFINITY | 0.473 | 1.51680 | 64.20 | Second Filter |
| IMAGE | INFINITY | 0.000 | | | |

In Table 8, the first lens 951 has first and second optical surfaces that are convex-concave, the third lens 953 has sixth and seventh optical surfaces that are planar-convex, and the fourth lens 954 has eighth and ninth optical surfaces that are bi-convex. The second lens 952 is a triangular prism, and has an object-side third optical surface and an image-side fourth optical surface that are bi-planar and also has a reflecting surface between the third optical surface and the fourth optical surface to bend an optical axis. The fourth lens 954 and the fifth lens 955 are double cemented lenses, and the fifth lens 955 has ninth and tenth optical surfaces that are concave-planar.

The first filter 956 has an object-side eleventh optical surface and an image-side twelfth optical surface that are bi-planar. The second filter 957 has an object-side thirteenth optical surface and an image surface which are bi-planar.

Figure 28:
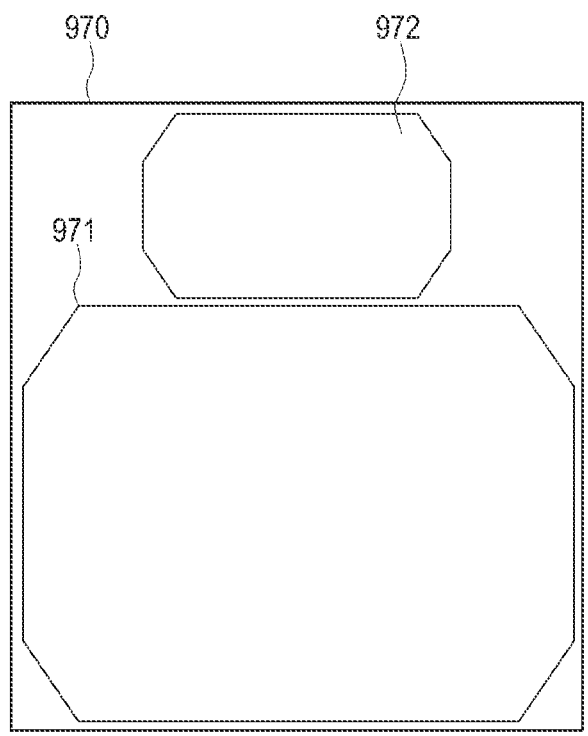

FIG. 28 is a diagram illustrating a screen 970 of the display 150 according to the fourth embodiment of the present invention. On the screen 970, a front-view region 971 displaying an image captured by the front-view optical system 910 and a side-view region 972 displaying an image captured by the side-view optical system 940 are provided.

By increasing a viewing angle of the front-view optical system 910, a lesion detection region of the front-view optical system 910 may be expanded and a lesion in a curved portion of a large intestine may be detected by the side-view optical system 940. Furthermore, by simply rotating the front end portion of the endoscope apparatus 900, observation along the circumference of the curved portion of the large intestine may be made easy. Moreover, even if the outer diameter of the front-view optical system 910 increases due to an increase of the viewing angle, the front end portion of the endoscope apparatus 900 may be miniaturized by providing the endoscope with one side-view optical system 940.

Table 9 provided below shows IH1/P1, IH1/EFL1, IH2/P2, and IH2/EFL2 of the above-described embodiments.

TABLE 9

|  | IH1/P1 | IH1/EFL1 | IH2/P2 | IH2/EFL2 |
|---|---|---|---|---|
| Embodiment 1 | 643 | 1.050 | 347 | 0.987 |
| Embodiment 2 | 369 | 1.020 | 279 | 0.780 |
| Embodiment 3 | 556 | 0.970 | 308 | 0.980 |
| Embodiment 4 | 744 | 1.209 | 588 | 1.050 |

Table 10 provided below shows limit resolutions of the above-described embodiments.

TABLE 10

|  | R1 | R2 | R3 | R4 | R5 |
|---|---|---|---|---|---|
| Embodiment 1 | 2.78 | 4.76 | 3.33 | 33.33 | 20.00 |
| Embodiment 2 | 2.38 | 4.00 | 3.57 | 33.33 | 20.00 |
| Embodiment 3 | 2.78 | 4.55 | 2.86 | 41.67 | 14.29 |
| Embodiment 4 | 2.94 | 5.26 | 4.55 | 33.33 | 19.23 |

Herein, the term "the resolution or limit resolution of an optical system" is used, but it may also be referred to as "the resolution or limit resolution of a lens system". According to the present invention, the endoscope apparatus provides an ultra-wide range observation optical system allowing observation of lesions in the curved portion of the wall in the tube of the large intestine, makes it easy to detect a lesion in screening, facilitates magnified observation of the lesion, and reduces the diameter of the front end portion of the endoscope apparatus.

It can be seen that the various embodiments of the present invention may be implemented with hardware, software, or a combination of hardware and software. Such arbitrary software may be stored, whether or not erasable or re-recordable, in a volatile or non-volatile storage such as a Read-Only Memory (ROM); a memory such as a Random Access Memory (RAM), a memory chip, a device, or an integrated circuit; and an optically or magnetically recordable and machine (for example, computer)-readable storage medium such as a Compact Disc (CD), a Digital Versatile Disk (DVD), a magnetic disk, or a magnetic tape. It can be seen that a memory included in the endoscope system is an example of a machine-readable recording medium that is suitable for storing a program or programs including instructions for implementing the various embodiments of the present invention. Therefore, the present invention includes a program including codes for implementing an apparatus or method claimed in an arbitrary claim and a machine-readable storage medium for storing such a program. The program may be electronically transferred through an arbitrary medium such as a communication signal delivered through wired or wireless connection, and the present invention properly includes equivalents thereof.

The endoscope system may receive and store the program from a program providing device connected in a wired or wireless manner. The program providing device may include a memory for storing a program including instructions for instructing the endoscope system to execute the claimed observation method using the preset endoscope apparatus, a memory for storing information necessary for observation using the endoscope apparatus, a communication unit for performing wired or wireless communication with the endoscope system, and a controller for transmitting a corresponding program to the endoscope system at the request of the endoscope system or automatically.

While the present invention has been particularly shown and described with reference to certain embodiments thereof, various changes in form and detail may be made therein without departing from the spirit and scope of the present invention as defined by the following claims. Accordingly, the scope of the present invention will be defined by the appended claims and equivalents thereto.

What is claimed is:

1. An endoscope apparatus comprising:
a first optical system comprising a first set of lenses configured to form a first optical image of a first object and a first image sensor configured to convert the first optical image into first image data and output the first image data; and
a second optical system comprising a second set of lenses configured to form a second optical image of a second object and a second image sensor configured to convert the second optical image into second image data and output the second image data,
wherein the first optical system satisfies a condition of 350<IH1/P1<800 and 0.95<IH1/EFL1<1.3, and
the second optical system satisfies a condition of 250<IH2/P2<600 and 0.7<IH2/EFL2<1.2,
in which IH1 denotes a maximum image height on an image surface of the first image sensor, IH2 denotes a maximum image height on an image surface of the second image sensor, P1 denotes a pixel pitch of the first image sensor, P2 denotes a pixel pitch of the second image sensor, EFL1 denotes a focal length of the first optical system, and EFL2 denotes a focal length of the second optical system, and
wherein each of the first set of lenses and the second set of lenses includes a stop having an aperture, and the second set of lenses includes a prism having a reflecting surface.

2. The endoscope apparatus of claim 1, wherein the endoscope apparatus satisfies a condition of R2>R3>R1,
in which R1 denotes a reciprocal of a minimum width of a pair of black and white lines that are recognizable by the first optical system at an object distance of 50 mm, R2 denotes a reciprocal of a minimum width of a pair of black and white lines that are recognizable by the first optical system at an object distance of 30 mm, and R3 denotes a reciprocal of a minimum width of a pair of black and white lines that are recognizable by the second optical system at the object distance of 30 mm.

3. The endoscope apparatus of claim 1, wherein the endoscope apparatus satisfies a condition of R4>R5,
in which R4 denotes a reciprocal of a minimum width of a pair of black and white lines that are recognizable by the second optical system at a minimum object distance, and R5 denotes a reciprocal of a minimum width of a pair of black and white lines that are recognizable by the first optical system at a minimum object distance corresponding to R4.

4. The endoscope apparatus of claim 1, wherein the first optical system is a front-view optical system configured to detect an image of an object situated in front of the endoscope apparatus, and wherein the second optical system is a side-view optical system configured to detect an image of an object situated at a side of the endoscope apparatus.

5. The endoscope apparatus of claim 4, further comprising at least one side-view optical system arranged along a circumference of the first optical system.

6. An endoscope apparatus comprising:

a first optical system comprising a first set of lenses configured to form a first optical image of a first object and a first image sensor configured to convert the first optical image into first image data and output the first image data; and a second optical system comprising a second set of lenses configured to form a second optical image of a second object and a second image sensor configured to convert the second optical image into second image data and output the second image data, wherein the endoscope apparatus satisfies a condition of R2>R3>R1, in which R1 denotes a reciprocal of a minimum width of a pair of black and white lines that are recognizable by the first optical system at an object distance of 50 mm, R2 denotes a reciprocal of a minimum width of a pair of black and white lines that are recognizable by the first optical system at an object distance of 30 mm, and R3 denotes a reciprocal of a minimum width of a pair of black and white lines that are recognizable by the second optical system at the object distance of 30 mm, and wherein each of the first set of lenses and the second set of lenses includes a stop having an aperture, and the second set of lenses includes a prism having a reflecting surface.

7. The endoscope apparatus of claim 6, wherein the endoscope apparatus satisfies a condition of R4>R5, in which R4 denotes a reciprocal of a minimum width of a pair of black and white lines that are recognizable by the second optical system at a minimum object distance, and R5 denotes a reciprocal of a minimum width of a pair of black and white lines that are recognizable by the first optical system at a minimum object distance corresponding to R4.

8. The endoscope apparatus of claim 6, wherein the first optical system satisfies a condition of $350<IH1/P1<800$ and $0.95<IH1/EFL1<1.3$, and the second optical system satisfies a condition of $250<IH2/P2<600$ and $0.7<IH2/EFL2<1.2$, in which IH1 denotes a maximum image height on an image surface of the first image sensor, IH2 denotes a maximum image height on an image surface of the second image sensor, P1 denotes a pixel pitch of the first image sensor, P2 denotes a pixel pitch of the second image sensor, EFL1 denotes a focal length of the first optical system, and EFL2 denotes a focal length of the second optical system.

9. The endoscope apparatus of claim 6, wherein the first optical system is a front-view optical system configured to detect an image of an object situated in front of the endoscope apparatus, and wherein the second optical system is a side-view optical system configured to detect an image of an object situated at a side of the endoscope apparatus.

10. The endoscope apparatus of claim 9, further comprising at least one side-view optical system arranged along a circumference of the first optical system.

* * * * *